(12) United States Patent
Hebrink et al.

(10) Patent No.: US 7,459,204 B2
(45) Date of Patent: *Dec. 2, 2008

(54) MODIFIED COPOLYESTERS AND IMPROVED MULTILAYER REFLECTIVE FILMS

(75) Inventors: Timothy J. Hebrink, Oakdale, MN (US); William W. Merrill, White Bear Lake, MN (US); Carl A. Stover, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/611,462

(22) Filed: Dec. 15, 2006

(65) Prior Publication Data

US 2007/0098970 A1    May 3, 2007

Related U.S. Application Data

(60) Division of application No. 11/171,057, filed on Jun. 30, 2005, now Pat. No. 7,150,907, which is a continuation of application No. 10/676,692, filed on Oct. 1, 2003, now Pat. No. 6,946,188, which is a continuation of application No. 09/996,655, filed on Nov. 28, 2001, now Pat. No. 6,641,900, which is a continuation of application No. 09/232,332, filed on Jan. 15, 1999, now Pat. No. 6,352,761, which is a continuation-in-part of application No. 09/006,601, filed on Jan. 13, 1998, now abandoned.

(51) Int. Cl.
*B32B 7/02* (2006.01)
*B32B 27/08* (2006.01)
*B32B 27/36* (2006.01)

(52) U.S. Cl. .............. 428/212; 428/480; 428/910; 528/302; 528/305; 528/307; 528/308; 528/308.6; 359/485; 359/487; 359/494; 359/500; 359/577; 359/586

(58) Field of Classification Search ............ None
See application file for complete search history.

(56) References Cited

U.S. PATENT DOCUMENTS 2,803,552 A    8/1957    Stedman (Continued)

FOREIGN PATENT DOCUMENTS

CZ    164399    11/1975

(Continued)

OTHER PUBLICATIONS

Fenoglio, D.J. et al., "The Effect of the t-Butyl Substituent on Polymer Properties in Homopolymer Systems", Journal of Polymer Science: Part A: Polymer Chemistry, vol. 28, pp. 2753-2764 (1990).

(Continued)

*Primary Examiner*—Vivian Chen
(74) *Attorney, Agent, or Firm*—Carolyn A. Fischer

(57) ABSTRACT

A multilayered polymer film includes a first set of optical layers and a second set of optical layers. The first set of optical layers is made from a polyester which is often birefringent. The polyesters of the first set of optical layers typically have a composition in which 70-100 mol % of the carboxylate subunits are first carboxylate subunits and 0-30 mol % are comonomer carboxylate subunits and 70 to 100 mol % of the glycol subunits are first glycol subunits and 0 to 30 mol % of the glycol subunits are comonomer glycol subunits, where at least 0.5 mol % of the combined carboxylate and glycol subunits are comonomer carboxylate or comonomer glycol subunits. The multilayered polymer film may be used to form, for example, a reflective polarizer or a mirror.

12 Claims, 6 Drawing Sheets

U.S. PATENT DOCUMENTS

| | | |
|---|---|---|
| 3,022,178 A | 8/1962 | Park et al. |
| 3,075,228 A | 1/1963 | Elias |
| 3,124,639 A | 3/1964 | Kahn |
| 3,212,909 A | 10/1965 | Leigh |
| 3,492,274 A | 1/1970 | Lederman et al. |
| 3,610,729 A | 10/1971 | Rogers |
| 3,629,202 A | 12/1971 | Gilkey et al. |
| 3,711,176 A | 1/1973 | Alfrey, Jr. et al. |
| 3,819,522 A | 6/1974 | Zmoda |
| 3,860,036 A | 1/1975 | Newman, Jr. |
| 3,897,356 A | 7/1975 | Pociluyko |
| 4,094,721 A * | 6/1978 | Sturm et al. ............. 156/306.6 |
| 4,249,011 A | 2/1981 | Wendling |
| 4,310,584 A | 1/1982 | Cooper et al. |
| 4,313,903 A * | 2/1982 | Bier ........................ 264/328.1 |
| 4,362,839 A * | 12/1982 | Tonoki et al. ............... 524/513 |
| 4,435,546 A * | 3/1984 | Bier et al. .................... 525/418 |
| 4,446,305 A | 5/1984 | Rogers et al. |
| 4,478,909 A | 10/1984 | Taniguchi et al. |
| 4,489,110 A * | 12/1984 | Bier .......................... 427/250 |
| 4,520,189 A | 5/1985 | Rogers et al. |
| 4,521,588 A | 6/1985 | Rogers et al. |
| 4,525,413 A | 6/1985 | Rogers et al. |
| 4,535,124 A * | 8/1985 | Binsack et al. ................. 525/67 |
| 4,720,426 A | 1/1988 | Englert et al. |
| 5,039,760 A * | 8/1991 | Nakane et al. ............... 525/448 |
| 5,188,760 A | 2/1993 | Hikmet et al. |
| 5,211,878 A | 5/1993 | Reiffenrath et al. |
| 5,235,443 A | 8/1993 | Barnik et al. |
| 5,269,995 A | 12/1993 | Ramanathan et al. |
| 5,294,657 A | 3/1994 | Melendy et al. |
| 5,316,703 A | 5/1994 | Schrenk |
| 5,319,478 A | 6/1994 | Fijnfschilling et al. |
| 5,389,324 A | 2/1995 | Lewis et al. |
| 5,448,404 A | 9/1995 | Schrenk et al. |
| 5,486,935 A | 1/1996 | Kalmanash |
| 5,486,949 A | 1/1996 | Schrenk et al. |
| 5,612,820 A | 3/1997 | Schrenk et al. |
| 5,629,055 A | 5/1997 | Revol et al. |
| 5,656,356 A | 8/1997 | Masuda et al. |
| 5,686,979 A | 11/1997 | Weber et al. |
| 5,699,188 A | 12/1997 | Gilbert et al. |
| 5,721,603 A | 2/1998 | De Vaan et al. |
| 5,744,534 A | 4/1998 | Ishiharada et al. |
| 5,751,388 A | 5/1998 | Larson |
| 5,759,467 A | 6/1998 | Carter et al. |
| 5,767,935 A | 6/1998 | Ueda et al. |
| 5,770,306 A | 6/1998 | Suzuki et al. |
| 5,783,120 A | 7/1998 | Ouderkirk et al. |
| 5,793,456 A | 8/1998 | Broer et al. |
| 5,808,794 A | 9/1998 | Weber et al. |
| 5,825,542 A | 10/1998 | Cobb, Jr. et al. |
| 5,825,543 A | 10/1998 | Ouderkirk et al. |
| 5,867,316 A | 2/1999 | Carlson et al. |
| 5,882,774 A | 3/1999 | Jonza et al. |
| 5,940,149 A | 8/1999 | Vanderwerf |
| 5,962,114 A | 10/1999 | Jonza et al. |
| 5,965,247 A | 10/1999 | Jonza et al. |
| 5,976,424 A | 11/1999 | Weber et al. |
| 5,999,316 A | 12/1999 | Allen et al. |
| 6,012,820 A | 1/2000 | Weber et al. |
| 6,045,894 A | 4/2000 | Jonza et al. |
| 6,049,419 A | 4/2000 | Wheatley et al. |
| 6,057,961 A | 5/2000 | Allen et al. |
| 6,088,067 A | 7/2000 | Willett et al. |
| 6,088,163 A | 7/2000 | Gilbert et al. |
| 6,101,032 A | 8/2000 | Wortman et al. |
| 6,111,696 A | 8/2000 | Allen et al. |
| 6,111,697 A | 8/2000 | Merrill et al. |
| 6,113,811 A | 9/2000 | Kausch et al. |
| 6,124,971 A | 9/2000 | Ouderkirk et al. |
| 6,288,172 B1 | 9/2001 | Goetz et al. |
| 6,297,906 B1 | 10/2001 | Allen et al. |
| 6,307,676 B1 | 10/2001 | Merrill et al. |
| 6,322,236 B1 | 11/2001 | Campbell et al. |
| 6,352,761 B1 | 3/2002 | Hebrink et al. |
| 6,449,093 B2 | 9/2002 | Hebrink et al. |
| 6,569,515 B2 | 5/2003 | Hebrink et al. |
| 6,609,795 B2 | 8/2003 | Weber et al. |
| 6,641,900 B2 | 11/2003 | Hebrink et al. |
| 6,946,188 B2 | 9/2005 | Hebrink et al. |
| 7,052,762 B2 * | 5/2006 | Hebrink et al. ............. 428/212 |
| 7,150,907 B2 * | 12/2006 | Hebrink et al. ............. 428/212 |
| 2002/0005986 A1 | 1/2002 | Hebrink et al. |
| 2002/0122252 A1 | 9/2002 | Hebrink et al. |
| 2003/0072931 A1 | 4/2003 | Hebrink et al. |

FOREIGN PATENT DOCUMENTS

| | | |
|---|---|---|
| EP | 0 489 482 | 6/1992 |
| EP | 0 591 055 | 9/1993 |
| EP | 0 592 284 | 9/1993 |
| JP | HEI 6 41335 | 2/1994 |
| WO | WO 95/17303 | 6/1995 |
| WO | WO 95/17691 | 6/1995 |
| WO | WO 95/17692 | 6/1995 |
| WO | WO 95/17699 | 6/1995 |
| WO | WO 95/27919 | 4/1996 |
| WO | WO 96/18691 | 6/1996 |
| WO | WO 96/19347 | 6/1996 |
| WO | WO 97/01440 | 1/1997 |
| WO | WO 97/01726 | 1/1997 |
| WO | WO 97/01774 | 1/1997 |
| WO | WO 97/01778 | 1/1997 |
| WO | WO 97/32223 | 9/1997 |
| WO | WO 97/32226 | 9/1997 |

OTHER PUBLICATIONS

Schrenk et al., Nanolayer polymeric optical films, Tappi Journal, pp. 169-174, Jun. 1992.

Vieweg et al., Polyester, Kunststoff-Handbuch, vol. VII (1973), p. 702.

John Wiley & Sons, New York, Encyclopedia of Polymer Science and Engineering, vol. 14, pp. 288-291 (1988).

* cited by examiner

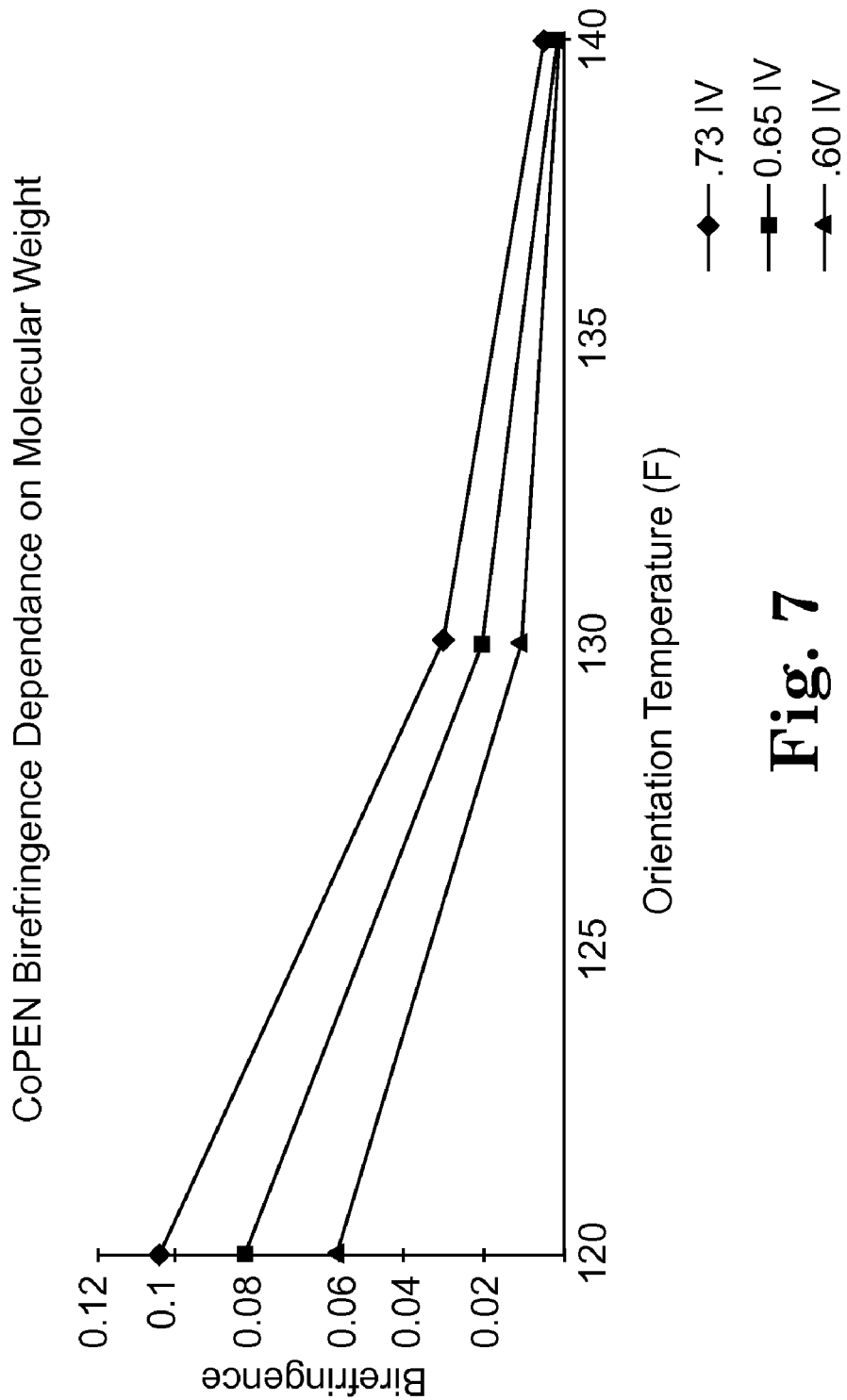

MODIFIED COPOLYESTERS AND IMPROVED MULTILAYER REFLECTIVE FILMS

This application is a divisional of Ser. No. 11/171,057, filed Jun. 30, 2005, now U.S. Pat. No. 7,150,907; which is a continuation of U.S. patent application Ser. No. 10/676,692, filed Oct. 1, 2003, now U.S. Pat. No. 6,946,188; which is a continuation of U.S. patent application Ser. No. 09/996,655, filed Nov. 28, 2001, now U.S. Pat. No. 6,641,900; which is a continuation of U.S. patent application Ser. No. 09/232,332, filed Jan. 15, 1999, now U.S. Pat. No. 6,352,761; which is a continuation-in-part of U.S. application Ser. No. 09/006,601, filed Jan. 13, 1998, now abandoned.

FIELD OF THE INVENTION

The present invention relates to multilayer optical films having two or more different sets of layers, each set being formed from a different polyester, and to improved polyesters for use in these films.

BACKGROUND OF THE INVENTION

Polymeric films are used in a wide variety of applications. One particular use of polymeric films is in mirrors and polarizers that reflect light of a given polarization and wavelength range. Such reflective films are used, for example, in conjunction with backlights in liquid crystal displays to enhance brightness and reduce glare of the display. A polarizing film may be placed between the user and the backlight to direct the light towards the user and to polarize the light; thereby reducing the glare. In addition, a mirror film may be placed behind the backlight to reflect light towards the user; thereby enhancing brightness. Another use of polarizing films is in articles, such as sunglasses, to reduce light intensity and glare.

One type of polymer that is useful in creating polarizer or mirror films is a polyester. One example of a polyester-based polarizer includes a stack of polyester layers of differing composition. One configuration of this stack of layers includes a first set of birefringent layers and a second set of layers with an isotropic index of refraction. The second set of layers alternates with the birefringent layers to form a series of interfaces for reflecting light. The polarizer may also include one or more non-optical layers which, for example, cover at least one surface of the stack of layers to prevent damage to the stack during or after processing. There are other configurations that may also be used in polarizer/mirror films including stacks of layers with two or more different sets of birefringent and/or isotropic layers.

The properties of a given polyester are typically determined by the monomer materials utilized in the preparation of the polyester. A polyester is often prepared by reactions of one or more different carboxylate monomers (e.g., compounds with two or more carboxylic acid or ester functional groups) with one or more different glycol monomers (e.g., compounds with two or more hydroxy functional groups). Each set of polyester layers in the stack typically has a different combination of monomers to generate the desired properties for each type of layer. There is a need for the development of polyester films for use in polarizers and mirrors which have improved properties including physical properties, optical properties, and lower manufacturing cost.

SUMMARY OF THE INVENTION

Generally, the present invention relates to a multilayered polymer film. One embodiment is a multilayered polymer film which includes a plurality of first layers and a plurality of second layers. The first layers are made with a first copolyester which is semicrystalline and birefringent. The first copolyester includes carboxylate subunits and glycol subunits in which 70 to 100 mol % of the carboxylate subunits are first carboxylate subunits, 0 to 30 mol % of the carboxylate subunits are first comonomer carboxylate subunits, 70 to 100 mol % of the glycol subunits are first glycol subunits, and 0 to 30 mol % of the glycol subunits are first comonomer glycol subunits, and at least 2.5 mol % of the combined carboxylate and glycol subunits of the first copolyester are first comonomer carboxylate subunits, first comonomer glycol subunits, or a combination thereof. The second layers are made with a second polymer which has an in-plane birefringence of about 0.04 or less, at 632.8 nm, after the multilayered polymer film has been formed.

Another embodiment is a multilayered polymer film having a plurality of first layers and a plurality of second layers. The first layers are made with a first copolyester which is semicrystalline and birefringent. The first copolyester includes carboxylate subunits and glycol subunits in which 70 to 100 mol % of the carboxylate subunits are first carboxylate subunits, 0 to 30 mol % of the carboxylate subunits are first comonomer carboxylate subunits, 70 to 100 mol % of the glycol subunits are first glycol subunits, 0 to 30 mol % of the glycol subunits are first comonomer glycol subunits, and at least 0.5 mol % of the combined carboxylate and glycol subunits of the first copolyester are first comonomer carboxylate subunits, first comonomer glycol subunits, or a combination thereof. The first copolyester has in-plane indices of refraction which are 1.83 or less and which differ by 0.2 or greater when measured with 632.8 nm light. The second layers are made with a second polymer which has an in-plane birefringence of about 0.04 or less at 632.8 nm after the multilayered polymer film has been formed.

A further embodiment is a multilayered polymer film which has a plurality of first layers and a plurality of second layers. The first layers are made with a first copolyester which is semicrystalline and birefringent. The first copolyester has carboxylate subunits and glycol subunits in which 70 to 100 mol % of the carboxylate subunits are first carboxylate subunits, 0 to 30 mol % of the carboxylate subunits are first comonomer carboxylate subunits, 70 to 100 mol % of the glycol subunits are first glycol subunits, 0 to 30 mol % of the glycol subunits are first comonomer glycol subunits, and at least 0.5 mol % of the combined carboxylate and glycol subunits of the first copolyester are first comonomer carboxylate subunits, first comonomer glycol subunits, or a combination thereof. The second layers are made with a second polymer having an in-plane birefringence of about 0.04 or less at 632.8 nm after the multilayered polymer film has been formed. The multilayered polymer film is formed by drawing the first and second layers in at least one draw direction to a particular draw ratio. After drawing the first and second layers, the first layers of the multilayered polymer film have an index of refraction in the draw direction which, at 632.8 nm, is at least 0.02 units less than an index of refraction in the draw direction of a similarly constructed polyethylene naphthalate layer which has a same in-plane birefringence and draw ratio.

Yet another embodiment is a multilayered polymer film which includes a plurality of first layers and a plurality of second layers. The first layers are made with a first copolyester which is semicrystalline and birefringent. The first copolyester has carboxylate subunits and glycol subunits in which 70 to 100 mol % of the carboxylate subunits are first carboxylate subunits, 70 to 99 mol % of the glycol subunits are first glycol subunits, and 1 to 30 mol % of the glycol subunits are first comonomer glycol subunits. The second layers are made with a second polymer which has an in-plane birefringence of about 0.04 or less, at 632.8 nm, after the multilayered polymer film has been formed.

Another embodiment is a multilayered polymeric film which has a plurality of first layers and a plurality of second layers. The first layers are made with a first copolyester which is semicrystalline and birefringent. The second layers are made with a second copolyester which has an in-plane birefringence of about 0.04 or less, at 632.8 nm, after the multilayered polymer film has been formed. The second copolyester includes carboxylate subunits and glycol subunits in which 0.01 to 2.5 mol % of the combined carboxylate and glycol subunits are derived from compounds with three or more carboxylate or ester functional groups, compounds with three or more hydroxy functional groups, or a combination thereof.

A further embodiment is a multilayer polymer film which includes a plurality of first layers and a plurality of second layers. The first layers are made with a first copolyester which is semicrystalline and birefringent. The second layers are made with a second copolyester of polyethylene naphthalate. The second copolyester includes glycol subunits and carboxylate subunits in which the glycol subunits are 70 to 100 mol % ethylene or butylene subunits and about 0 to 30 mol % comonomer glycol subunits derived from one or more of 1,6-hexanediol, trimethylol propane, or neopentyl glycol, and the carboxylate subunits are 20 to 100 mol % naphthalate subunits, 0 to 80 mol % terephthalate or isophthalate subunits or mixtures thereof, and 0 to 30 mol % of comonomer carboxylate subunits derived from phthalic acid, t-butyl-isophthalic acid, lower alkyl esters of these acids, or a combination thereof, and at least 0.5 mol % of the combined carboxylate and glycol subunits of the second copolyester are comonomer carboxylate subunits, comonomer glycol subunits, or a combination thereof.

Another embodiment is a polymer which is a copolyester having an intrinsic viscosity of about 0.4 dL/g or greater as measured in a 60/40 wt. % mixture of phenol/o-dichlorobenzene. The polymer includes glycol subunits and carboxylate subunits in which the glycol subunits are 70 to 99 mol % ethylene or butylene subunits and 1 to 30 mol % comonomer glycol subunits derived from 1,6-hexanediol, and the carboxylate subunits are 5 to 99 mol % naphthalate subunits, 1 to 95 mol % terephthalate or isophthalate subunits or a combination thereof, and 0 to 30 mol % of comonomer carboxylate subunits derived from phthalic acid, t-butyl-isophthalic acid, lower alkyl esters of these acids, or a combination thereof, and at least 0.01 to 2.5 mol % of the combined carboxylate and glycol subunits of the copolyester are derived from compounds having three or more carboxylate, ester, or hydroxy functional groups.

One other embodiment is a multilayer polymer film which includes a plurality of birefringent first layers and a plurality of second layers. The first layers are made with a first copolyester having naphthalate subunits. The second layers are made with a second copolyester which has an intrinsic viscosity of 0.4 to 0.5 dL/g and contains 0.01 to 5 mol % comonomer subunits which are derived from compounds having three or more carboxylate, ester, or hydroxy functional groups. The multilayer polymer film also includes one or more non-optical layers that have an intrinsic viscosity of 0.5 dL/g or greater.

The above summary of the present invention is not intended to describe each illustrated embodiment or every implementation of the present invention. The figures and the detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 7 is a graph illustrating the dependence of in-plane birefringence, at 632.8 nm, on molecular weight.

Figure 1:
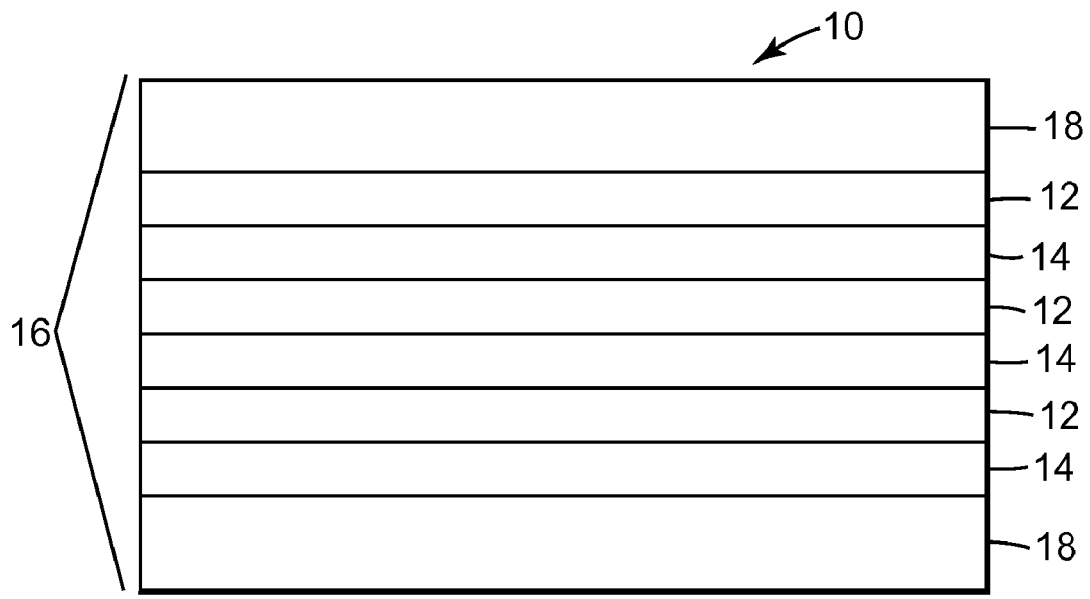
FIG. 1 is a cross-sectional view of one embodiment of a multilayered polymer film according to the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention relates to multilayered polymer films for optical applications and the use of comonomer subunits to enhance the properties of the polymer films and, in particular, to enhance the properties of polymer films made from polyesters having naphthalate subunits, including, for example, copolymers of polyethylene naphthalate.

FIG. 1 shows a multilayered polymer film 10 which may be used, for example, as an optical polarizer or mirror. The film 10 includes one or more first optical layers 12, one or more second optical layers 14, and one or more non-optical layers 18. The first optical layers 12 are preferably birefringent polymer layers which are uniaxially- or biaxially-oriented. The second optical layers 14 may also be polymer layers which are birefringent and uniaxially- or biaxially-oriented. More typically, however, the second optical layers 14 have an isotropic index of refraction which is different from at least one of the indices of refraction of the first optical layers 12 after orientation. The methods of manufacture and use, as well as design considerations for the multilayered polymer films 10 are described in detail in U.S. Pat. No. 5,882,774 entitled "Multilayered Optical Film" and U.S. patent application Ser. No. 09/006,288 entitled "Process for Making Multilayer Optical Film." Although, the present invention will be primarily exemplified by films 10 with second optical layers 14 which have an isotropic index of refraction, the principles and examples described herein may be applied to multilayered polymer films with second optical layers 14 that are birefringent, as described in U.S. Pat. No. 6,113,811, entitled "Optical Film and Process for the Manufacture Thereof."

Additional sets of optical layers, similar to the first and second optical layers 12, 14, may also be used in the multilayered polymer film 10. The design principles disclosed herein for the sets of first and second optical layers may be applied to any additional sets of optical layers. Furthermore, it will be appreciated that, although only a single stack 16 is illustrated in FIG. 1, the multilayered polymer film 10 may be made from multiple stacks that are subsequently combined to form the film 10.

The optical layers 12, 14 and, optionally, one or more of the non-optical layers 18 are typically placed one on top of the other to form a stack 16 of layers. Usually the optical layers 12, 14 are arranged as alternating pairs, as shown in FIG. 1, to form a series of interfaces between layers with different optical properties. The optical layers 12, 14 are typically less than 1 µm thick, although thicker layers may be used. Furthermore, although FIG. 1 shows only six optical layers 12, 14, many multilayered polymer films 10 have a large number of optical layers. Typical multilayered polymer films have about 2 to 5000 optical layers, preferably about 25 to 2000 optical layers, more preferably about 50 to 1500 optical layers, and most preferably about 75 to 1000 optical layers.

The non-optical layers 18 are polymer layers that are disposed within (see FIG. 2) and/or over (see FIG. 1) the stack 16 to protect the optical layers 12, 14 from damage, to aid in the co-extrusion processing, and/or to enhance post-processing mechanical properties. The non-optical layers 18 are often thicker than the optical layers 12, 14. The thickness of the non-optical layers 18 is usually at least two times, preferably at least four times, and more preferably at least ten times, the thickness of the individual optical layers 12, 14. The thickness of the non-optical layers 18 may be varied to make a multilayer polymer film 10 having a particular thickness. Typically, one or more of the non-optical layers 18 are placed so that at least a portion of the light to be transmitted, polarized, and/or reflected by the optical layers 12, 14, also travels through the non-optical layers (i.e., the non-optical layers are placed in the path of light which travels through or is reflected by the optical layers 12, 14).

The optical layers 12, 14 and the non-optical layers 18 of the multilayered polymer film 10 are typically composed of polymers such as polyesters. Polyesters include carboxylate and glycol subunits and are generated by reactions of carboxylate monomer molecules with glycol monomer molecules. Each carboxylate monomer molecule has two or more carboxylic acid or ester functional groups and each glycol monomer molecule has two or more hydroxy functional groups. The carboxylate monomer molecules may all be the same or there may be two or more different types of molecules. The same applies to the glycol monomer molecules. The term "polymer" will be understood to include both polymers and copolymers, as well as polymers or copolymers which may be formed in a miscible blend, for example, by coextrusion or by reaction, including, for example, transesterification.

The properties of a polymer layer or film vary with the particular choice of monomer molecules. One example of a polyester useful in multilayered optical films is polyethylene naphthalate (PEN) which can be made, for example, by reactions of naphthalene dicarboxylic acid with ethylene glycol.

Suitable carboxylate monomer molecules for use in forming the carboxylate subunits of the polyester layers include, for example, 2,6-naphthalene dicarboxylic acid and isomers thereof; terephthalic acid; isophthalic acid; phthalic acid; azelaic acid; adipic acid; sebacic acid; norbornene dicarboxylic acid; bi-cyclooctane dicarboxylic acid; 1,6-cyclohexane dicarboxylic acid and isomers thereof; t-butyl isophthalic acid, tri-mellitic acid, sodium sulfonated isophthalic acid; 2,2'-biphenyl dicarboxylic acid and isomers thereof; and lower alkyl esters of these acids, such as methyl or ethyl esters. The term "lower alkyl" refers, in this context, to C1-C10 straight-chained or branched alkyl groups. Also included within the term "polyester" are polycarbonates which are derived from the reaction of glycol monomer molecules with esters of carbonic acid.

Suitable glycol monomer molecules for use in forming glycol subunits of the polyester layers include ethylene glycol; propylene glycol; 1,4-butanediol and isomers thereof; 1,6-hexanediol; neopentyl glycol; polyethylene glycol; diethylene glycol; tricyclodecanediol; 1,4-cyclohexanedimethanol and isomers thereof, norbornanediol; bicyclo-octanediol; trimethylol propane; pentaerythritol; 1,4-benzenedimethanol and isomers thereof; bisphenol A; 1,8-dihydroxy biphenyl and isomers thereof; and 1,3-bis(2-hydroxyethoxy)benzene.

Non-polyester polymers are also useful in creating polarizer or mirror films. For example, layers made from a polyester such as polyethylene naphthalate may be combined with layers made from an acrylic polymer to form a highly reflective mirror film. In addition, polyether imides may also be used with polyesters, such as PEN and coPEN, to generate a multilayered optical film. Other polyester/non-polyester combinations, such as polybutylene terephthalate and polyvinyl chloride, may also be used.

The first optical layers 12 are typically orientable polymer films, such as polyester films, which may be made birefringent by, for example, stretching the first optical layers 12 in a desired direction or directions. The term "birefringent" means that the indices of refraction in orthogonal x, y, and z directions are not all the same. For films or layers in a film, a convenient choice of x, y, and z axes is shown in FIG. 1 in which the x and y axes correspond to the length and width of the film or layer and the z axis corresponds to the thickness of the layer or film. In the embodiment illustrated in FIG. 1, the film 10 has several optical layers 12, 14 which are stacked one on top of the other in the z-direction.

The first optical layers 12 may be uniaxially-oriented, for example, by stretching in a single direction. A second orthogonal direction may be allowed to neck into some value less than its original length. In one embodiment, the direction of stretching substantially corresponds to either the x or y axis shown in FIG. 1. However, other directions may be chosen. A birefringent, uniaxially-oriented layer typically exhibits a difference between the transmission and/or reflection of incident light rays having a plane of polarization parallel to the oriented direction (i.e., stretch direction) and light rays having a plane of polarization parallel to a transverse direction (i.e., a direction orthogonal to the stretch direction). For example, when an orientable polyester film is stretched along the x axis, the typical result is that $n_x \neq n_y$, where $n_x$ and $n_y$ are the indices of refraction for light polarized in a plane parallel to the "x" and "y" axes, respectively. The degree of alteration in the index of refraction along the stretch direction will depend on factors such as the amount of stretching, the stretch rate, the temperature of the film during stretching, the thickness of the film, the variation in the film thickness, and the composition of the film. Typically, the first optical layers 12 have an in-plane birefringence (the absolute value of $n_x - n_y$)

after orientation of 0.04 or greater at 632.8 nm, preferably about 0.1 or greater, and more preferably about 0.2 or greater. All birefringence and index of refraction values are reported for 632.8 nm light unless otherwise indicated.

Polyethylene naphthalate (PEN) is an example of a useful material for forming the first optical layers 12 because it is highly birefringent after stretching. The refractive index of PEN for 632.8 nm light polarized in a plane parallel to the stretch direction increases from about 1.62 to as high as about 1.87. Within the visible spectrum, PEN exhibits a birefringence of 0.20 to 0.40 over a wavelength range of 400-700 nm for a typical high orientation stretch (e.g., a material stretched to five or more times its original dimension at a temperature of 130° C. and an initial strain rate of 20%/min).

The birefringence of a material can be increased by increasing the molecular orientation. Many birefringent materials are crystalline or semicrystalline. The term "crystalline" will be used herein to refer to both crystalline and semicrystalline materials. PEN and other crystalline polyesters, such as polybutylene naphthalate (PBN), polyethylene terephthalate (PET) and polybutylene terephthalate (PBT) are examples of crystalline materials useful in the construction of birefringent film layers, such as is often the case for the first optical layers 12. In addition, some copolymers of PEN, PBN, PET, and PBT are also crystalline or semicrystalline. The addition of a comonomer to PEN, PBN, PET, or PBT may enhance other properties of the material including, for example, adhesion to the second optical layers 14 or the non-optical layers 18 and/or the lowering of the working temperature (i.e., the temperature for extrusion and/or stretching the film).

In some embodiments, the first optical layers 12 are made from a semicrystalline, birefringent copolyester which includes 70 to 99 mol % of a first carboxylate subunit and 1 to 30 mol %, and preferably 5 to 15 mol %, of comonomer carboxylate subunits. The comonomer carboxylate subunits may be one or more of the subunits indicated hereinabove. Preferred first carboxylate subunits include naphthalate and terephthalate.

If the polyester material of the first optical layers 12 contains more than one type of carboxylate subunit, then the polyester may be a block copolyester to enhance adhesion to other layers (e.g., the second optical layers 14 or non-optical layers 18) made from block copolymers having similar blocks. Random copolyesters may also be used.

In other embodiments, the first optical layers 12 are made from a semicrystalline, birefringent copolyester which includes 70 to 99 mol % of a first glycol subunit and 1 to 30 mol %, and preferably 5 to 30 mol % of comonomer glycol subunits. The comonomer glycol subunits may be one or more of the subunits indicated hereinabove. Preferred first glycol subunits are derived from C2-C8 diols. More preferred first glycol subunits are derived from ethylene glycol or 1,4-butanediol.

Yet other embodiments include first optical layers 12 where both of the carboxylate and glycol subunits include comonomer subunits. For these embodiments, typically at least 0.5 mol %, and preferably at least 2.5 mol %, of the combined carboxylate and glycol subunits are comonomer carboxylate subunits, comonomer glycol subunits, or a combination thereof.

With the increasing addition of comonomer carboxylate and/or glycol subunits, the index of refraction in the orientation direction, typically the largest index of refraction, often decreases. Based on such an observation, this might lead to a conclusion that the birefringence of the first optical layers will be proportionately affected. However, it has been found that the index of refraction in the transverse direction also decreases with the addition of comonomer subunits. This results in substantial maintenance of the birefringence.

Figure 3A:
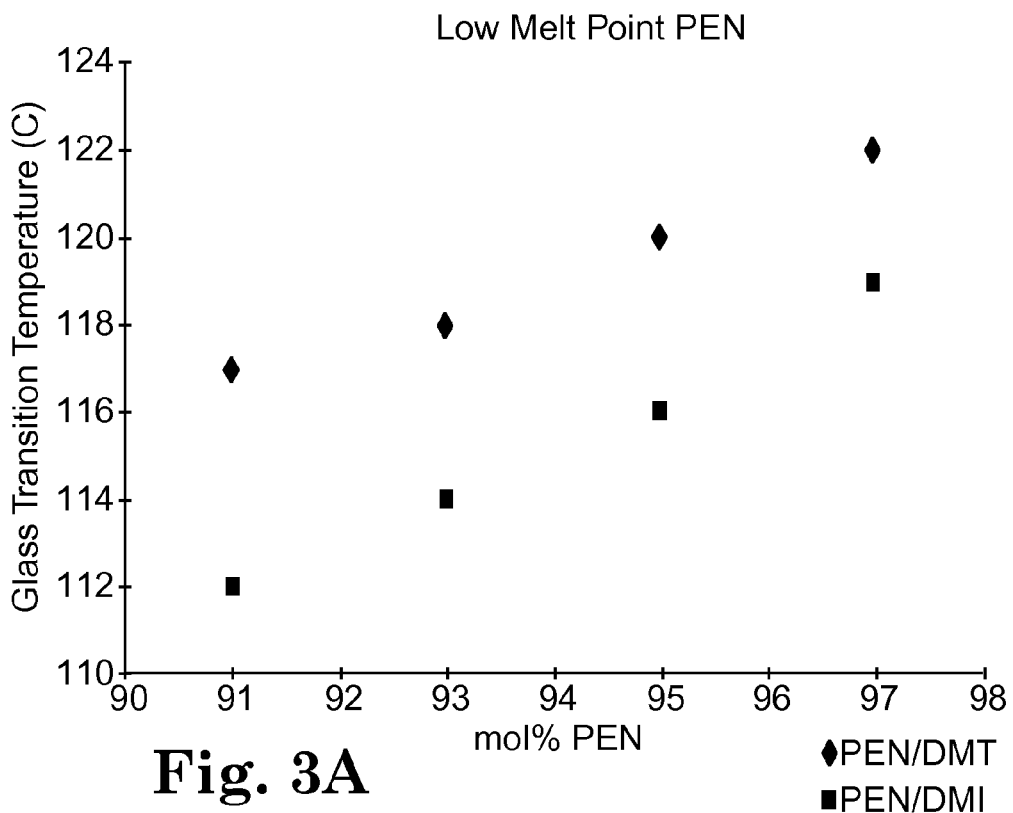
FIGS. 3A and 3B are graphs illustrating the decrease in glass transition temperature (FIG. 3A) and freezing temperature (FIG. 3B) with the addition of terephthalate (using dimethyl terephthalate (DMT)) and isophthalate (using dimethyl isophthalate (DMI)) subunits to polyethylene naphthalate (PEN) which is derived from dimethyl naphthalene dicarboxylate.
Figure 3B:
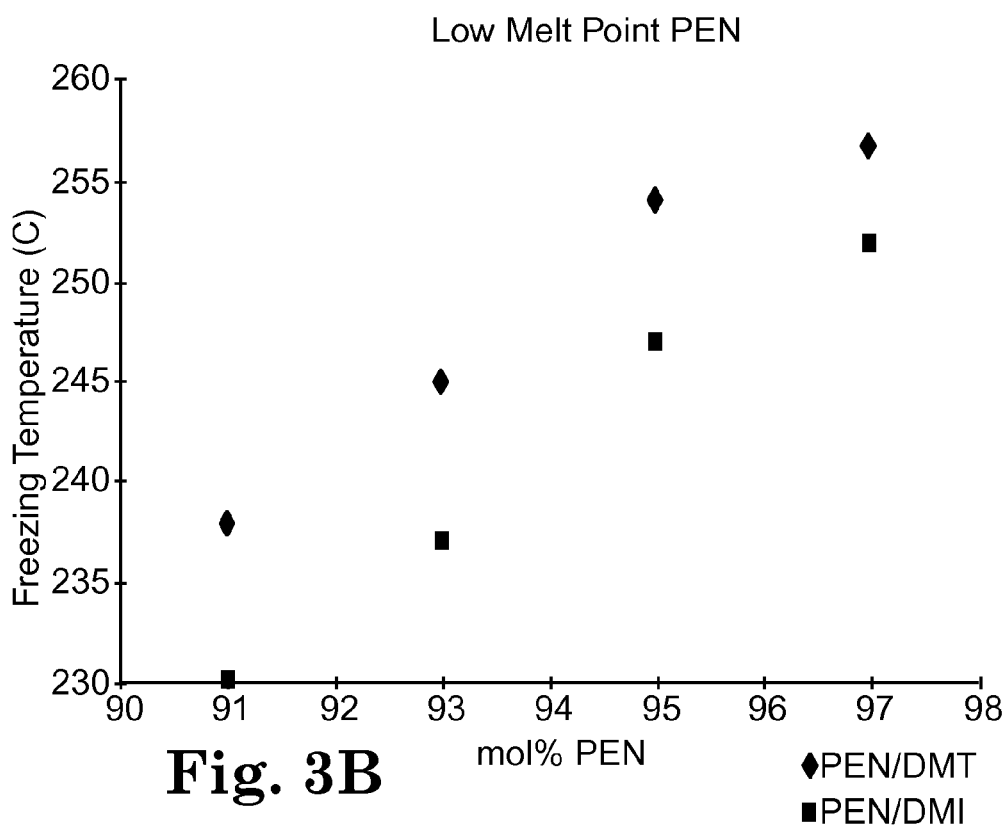
Figure 4:
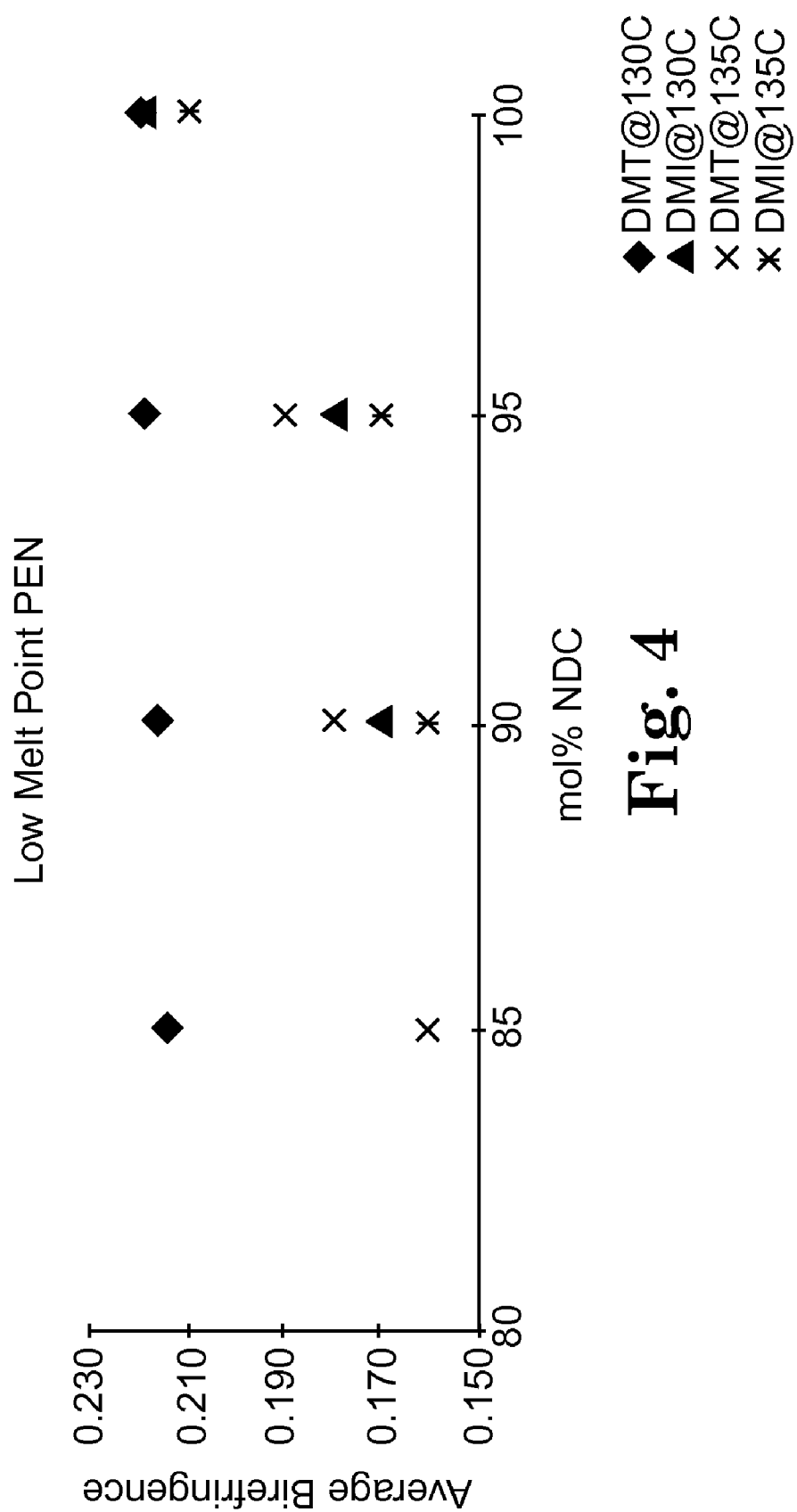
FIG. 4 is a graph of the average in-plane birefringence of coPEN modified with terephthalate and isophthalate subunits and oriented at relatively low temperatures.

For example, the addition of 3 mol % isophthalate subunits to polyethylene naphthalate reduces the melt processing temperature from about 280° C. to about 265° C. with only a 0.02 unit loss in birefringence. FIGS. 3A and 3B illustrate the reduction in glass transition temperature and freezing point temperature for the addition of 3 to 9 mol % isophthalate (derived from dimethyl isophthalate (DMI)) or terephthalate (derived from dimethyl terephthalate (DMT)) subunits. In general, the reduction in freezing point is typically greater than the change in the glass transition temperature for a given amount of substituted subunits. FIG. 4 illustrates the average birefringence of a low melt point coPEN having 0 to 9 mol % terephthalate and isophthalate subunits. This low melt point coPEN typically has better adhesion to second optical layers made from a coPEN which contains terephthalate and/or isophthalate subunits due to the presence of common monomer subunits.

In many cases, a multilayered polymer film 10 may be formed using first optical layers 12 that are made from a coPEN which has the same in-plane birefringence for a given draw ratio (i.e., the ratio of the length of the film in the stretch direction after stretching and before stretching) as a similar multilayered polymer film formed using PEN for the first optical layers. The matching of birefringence values may be accomplished by the adjustment of processing parameters, such as the processing or stretch temperatures. Often coPEN optical layers have an index of refraction in the draw direction which is at least 0.02 units less than the index of refraction of the PEN optical layers in the draw direction. The birefringence is maintained because there is a decrease in the index of refraction in the non-draw direction.

In some preferred embodiments of the multilayered polymer films, the first optical layers are made from a coPEN which has in-plane indices of refraction (i.e., $n_x$ and $n_y$) that are 1.83 or less, and preferably 1.80 or less, and which differ (i.e., $|n_x-n_y|$) by 0.15 units or more, and preferably 0.2 units or more, when measured using 632.8 nm light. PEN often has an in-plane index of refraction that is 1.84 or higher and the difference between the in-plane indices of refraction is about 0.22 to 0.24 or more when measured using 632.8 nm light. The in-plane refractive index differences, or birefringence, of the first optical layers, whether they be PEN or coPEN, may be reduced to less than 0.2 to improve properties, such as interlayer adhesion. Similar comparisons between suitable coPBN and coPET polymers for the first layers can be made with PBN and PET.

The second optical layers 14 may be made from a variety of polymers. Examples of suitable polymers include vinyl polymers and copolymers made from monomers such as vinyl naphthalenes, styrene, maleic anhydride, acrylates, and methacrylates. Examples of such polymers include polyacrylates, polymethacrylates, such as poly(methyl methacrylate) (PMMA), and isotactic or syndiotactic polystyrene. Other polymers include condensation polymers such as polysulfones, polyamides, polyurethanes, polyamic acids, and polyimides. In addition, the second optical layers 14 may be formed from polymers and copolymers such as polyesters and polycarbonates. The second optical layers 14 will be exemplified below by copolymers of polyesters. However, it will be understood that the other polymers described above may also be used. The same considerations with respect to optical properties for the copolyesters, as described below, will also typically be applicable for the other polymers and copolymers.

In some embodiments, the second optical layers 14 are uniaxially or biaxially orientable. However, more typically the second optical layers 14 are not oriented under the processing conditions used to orient the first optical layers 12. These second optical layers 14 typically retain a relatively isotropic index of refraction, even when stretched. Preferably, the second optical layers have a birefringence of less than about 0.04, and more preferably less than about 0.02 at 632.8 nm.

Examples of suitable materials for the second optical layers 14 are copolymers of PEN, PBN, PET, or PBT. Typically, these copolymers include carboxylate subunits which are 20 to 100 mol % second carboxylate subunits, such as naphthalate (for coPEN or coPBN) or terephthalate (for coPET or coPBT) subunits, and 0 to 80 mol % second comonomer carboxylate subunits. The copolymers also include glycol subunits which are 40 to 100 mol % second glycol subunits, such as ethylene (for coPEN or coPET) or butylene (for coPBN or coPBT), and 0 to 60 mol % second comonomer glycol subunits. At least about 10 mol % of the combined carboxylate and glycol subunits are second comonomer carboxylate or glycol subunits.

Figure 5:
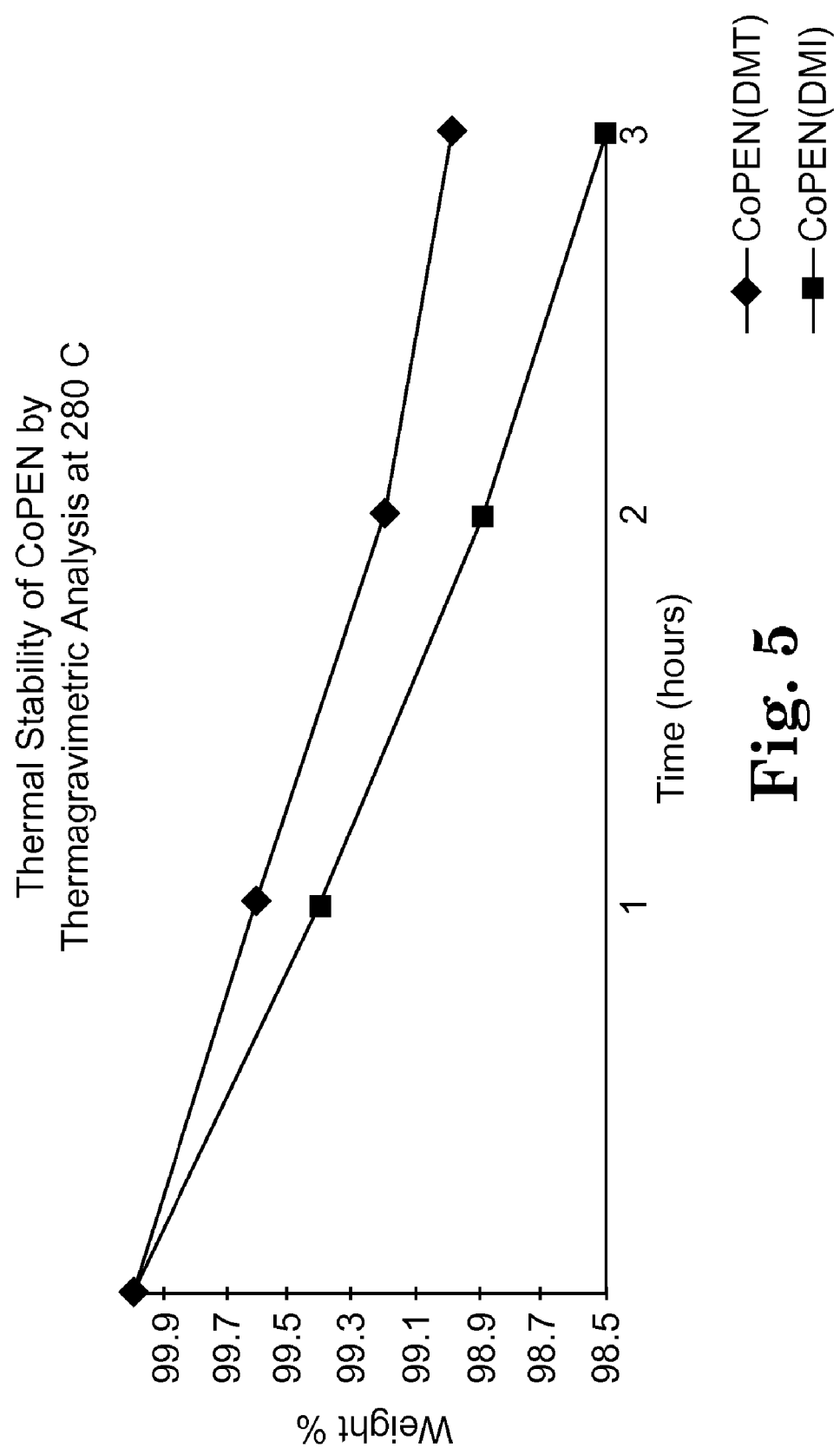
FIG. 5 is a graph of the thermal stability of coPEN containing terephthalate and isophthalate subunits.

One example of a polyester for use in second optical layers 14 is a low cost coPEN. One currently used coPEN has carboxylate subunits which are about 70 mol % naphthalate and about 30 mol % isophthalate. Low cost coPEN replaces some or all of the isophthalate subunits with terephthalate subunits. The cost of this polymer is reduced as dimethyl isophthalate, the typical source for the isophthalate subunits, currently costs considerably more than dimethyl terephthalate, a source for the terephthalate subunits. Furthermore, coPEN with terephthalate subunits tends to have greater thermal stability than coPEN with isophthalate subunits, as illustrated in FIG. 5.

However, substitution of terephthalate for isophthalate may increase the birefringence of the coPEN layer; so a combination of terephthalate and isophthalate may be desired. Low cost coPEN typically has carboxylate subunits in which 20 to 80 mol % of the carboxylate subunits are naphthalate, 10 to 60 mol % are terephthalate, and 0 to 50 mol % are isophthalate subunits. Preferably, 20 to 60% mol % of the carboxylate subunits are terephthalate and 0 to 20 mol % are isophthalate. More preferably, 50 to 70 mol % of the carboxylate subunits are naphthalate, 20 to 50 mol % are terephthalate, and 0 to 10 mol % are isophthalate subunits.

Figure 6:
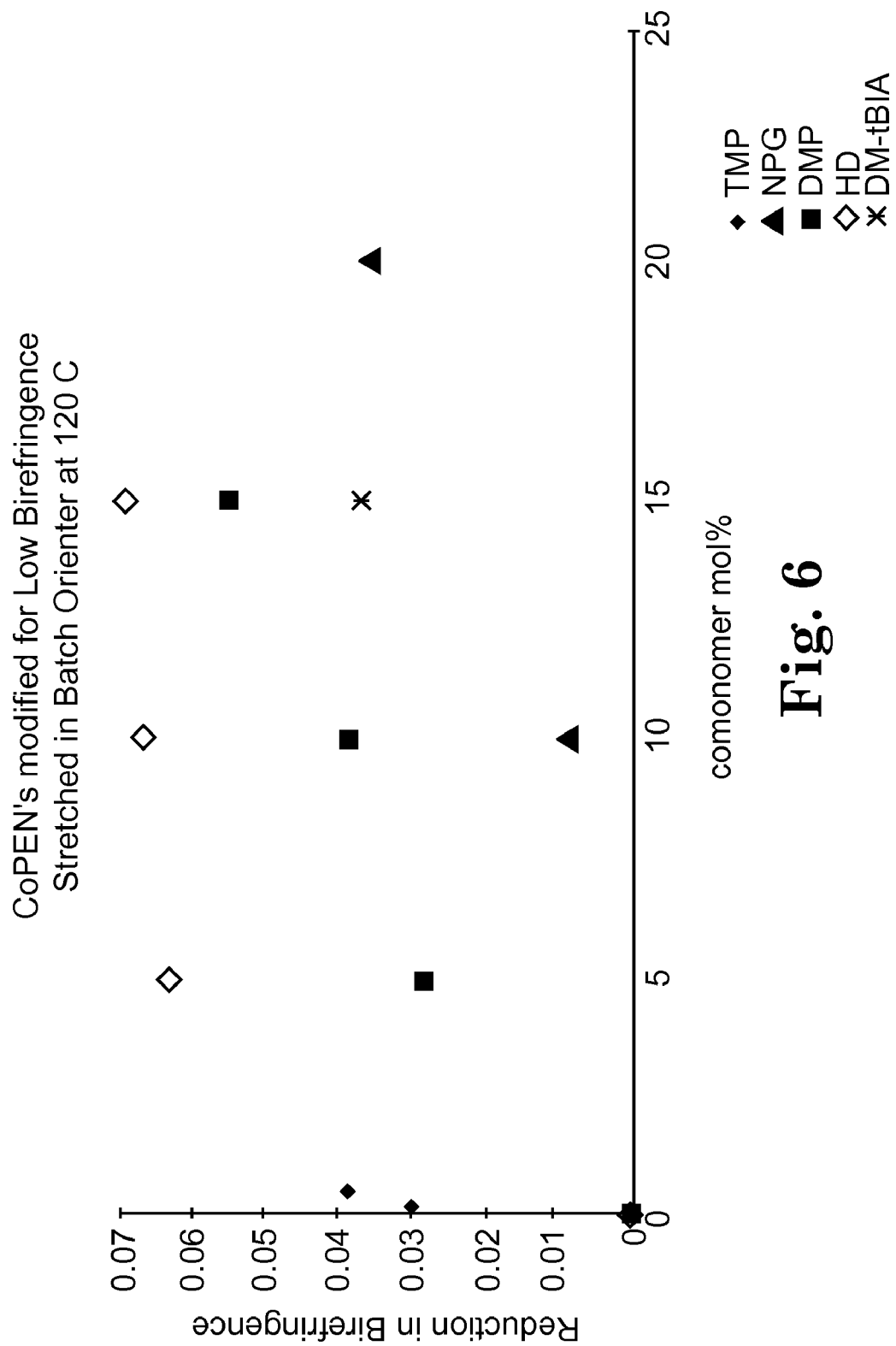
FIG. 6 is a graph illustrating the reduction in in-plane birefringence, at 632.8 nm, of a coPEN by the addition of comonomer subunits.

Because coPENs may be slightly birefringent and orient when stretched, it may be desirable to produce a polyester composition for use with second optical layers 14 in which this birefringence is reduced. Low birefringent coPENs may be synthesized by the addition of comonomer materials. Examples of suitable birefringent-reducing comonomer materials for use as diol subunits are derived from 1,6-hexanediol, trimethylol propane, and neopentyl glycol. Examples of suitable birefringent-reducing comonomer materials for use as carboxylate subunits are derived from t-butyl-isophthalic acid, phthalic acid, and lower alkyl esters thereof. FIG. 6 is a graph illustrating the reduction in birefringence of coPEN by addition of these materials. This reduction may be 0.07 or higher at 632.8 nm when the second optical layers 14 have been drawn under high strain conditions (e.g., at a draw ratio at 5:1 or greater) or under a low draw temperature. The addition of comonomers in the coPEN also increases the normal angle gain of the optical polarizer. Normal angle gain is a measure of the increase in light emitted from an LCD when the reflective polarizer is used in combination with an absorbing polymer.

Preferred birefringent-reducing comonomer materials are derived from t-butyl-isophthalic acid, lower alkyl esters thereof, and 1,6-hexanediol. Other preferred comonomer materials are trimethylol propane and pentaerythritol which may also act as branching agents. The comonomers may be distributed randomly in the coPEN polyester or they may form one or more blocks in a block copolymer.

Examples of low birefringent coPEN include glycol subunits which are derived from 70-100 mol % C2-C4 diols and about 0-30 mol % comonomer diol subunits derived from 1,6-hexanediol or isomers thereof, trimethylol propane, or neopentyl glycol and carboxylate subunits which are 20 to 100 mol % naphthalate, 0 to 80 mol % terephthalate or isophthalate subunits or mixtures thereof, and 0 to 30 mol % of comonomer carboxylate subunits derived from phthalic acid, t-butyl-isophthalic acid, or lower alkyl esters thereof. Furthermore, the low birefringence coPEN has at least 0.5 to 5 mol % of the combined carboxylate and glycol subunits which are comonomer carboxylate or glycol subunits.

The addition of comonomer subunits derived from compounds with three or more carboxylate, ester, or hydroxy functionalities may also decrease the birefringence of the copolyester of the second layers. These compounds act as branching agents to form branches or crosslinks with other polymer molecules. In some embodiments of the invention, the copolyester of the second layer includes 0.01 to 5 mol %, preferably 0.1 to 2.5 mol %, of these branching agents.

One particular polymer has glycol subunits that are derived from 70 to 99 mol % C2-C4 diols and about 1 to 30 mol % comonomer subunits derived from 1,6-hexanediol and carboxylate subunits that are 5 to 99 mol % naphthalate, 1 to 95 mol % terephthalate, isophthalate, or mixtures thereof, and 0 to 30 mol % comonomer carboxylate subunits derived from one or more of phthalic acid, t-butyl-isophthalic acid, or lower alkyl esters thereof. In addition, at least 0.01 to 2.5 mol % of the combined carboxylate and glycol subunits of this copolyester are branching agents.

Because birefringence typically decreases with molecular weight, another useful polyester is a low molecular weight coPEN. The low molecular weight coPEN has an intrinsic viscosity of 0.4 to 0.5 dL/g. The intrinsic viscosity of the polymer is retained by the addition of between about 0.5 to 5 mol % of monomers having three or more carboxylate, ester, and/or hydroxy groups. These monomers often act as branching agents. The molecular weight of the polymer is established by ending the polymerization at a specified melt viscosity determined by, for example, the power draw on a reactor agitator, agitator speed, and melt temperature. Typically, non-optical layers having an intrinsic viscosity of 0.5 dL/g or greater are used with this low molecular weight coPEN to provide structural support.

Suitable branching monomers for use in increasing the melt viscosity of a low molecular weight coPEN include alcohols with more than two hydroxy functionalities, as well as carboxylic acids with more than two carboxylic acid functionalities and lower alkyl esters thereof. Examples of suitable branching monomers include trimethylol propane, pentaerythritol, and trimellitic acid. FIG. 7 illustrates the decrease in birefringence with decrease in molecular weight (as measured by decrease in intrinsic viscosity).

Another type of useful copolyester includes cyclohexane dicarboxylate subunits. These copolyesters are especially useful as low refractive index polymers due to their viscoelastic properties which enable stable multilayer coextrusion with polyethylene naphthalate in the first optical layers 12. In contrast, some other aliphatic copolyesters with low refractive indices do not have the rheological properties necessary to provide stable melt flow when coextruded in a multilayer melt manifold with polyethylene naphthalate. Cyclohexane dicarboxylate also may provide improved thermal stability over other low refractive index copolyesters during coextrusion.

Tertiary-butyl isophthalate is a preferred carboxylate subunit for use with cyclohexane dicarboxylate in effectively improving the glass transition temperature and modulus of the copolyester without substantially increasing the refractive indices. The addition of tertiary-butyl isophthalate enables copolyesters of cyclohexane dicarboxylate to have glass transition temperatures above room temperature with refractive indices as low as 1.51 at 632.8 nm. Utilizing branching monomers such as trimethylol propane enables high viscosity polymers to be synthesized from these monomers without the need for large amounts of catalyst or long reaction times, which improves color and clarity of the polymer. Thus, non-birefringent copolyesters with low refractive indices may be produced with cyclohexane dicarboxylate and tertiary-butyl isophthalate providing the carboxylate subunits, and ethylene glycol and trimethylol propane providing the glycol subunits. These copolyesters are useful for making multilayer optical films which retain their physical properties at room temperature. Copolyesters made using naphthalene dicarboxylate and cyclohexane dicarboxylate as carboxylates can be coextruded with polyethylene naphthalate to form a multilayered polymer film with good interlayer adhesion.

One embodiment of the invention includes second optical layers made from a polyester with carboxylate subunits derived from cyclohexane dicarboxylate. Preferably, the polyester has carboxylate subunits derived from 5 to 95 mol % dimethyl cyclohexane dicarboxylate and 5 to 95 mol % dimethyl tertiary-butyl isophthalate and glycol subunits derived from 85 to 99.99 mol % C2-C4 diols and 0.01 to 5 mol % trimethylol propane. More preferably, the polyester has carboxylate subunits derived from 50 to 85 mol % dimethyl cyclohexane dicarboxylate and 15 to 50 mol % dimethyl tertiary-butyl isophthalate and glycol subunits derived from 98 to 99.99 mol % C2-C4 diols and 0.01 to 2 mol % trimethylol propane.

The non-optical layers 18 may also be made from copolyesters similar to the second optical layers 14, using similar materials and similar amounts of each material. In addition, other polymers may also be used, as described above with respect to the second optical layers 14. It has been found that the use of coPEN (i.e., a copolymer of PEN) or other copolymer material for skin layers (as seen in FIG. 1) reduces the splittiness (i.e., the breaking apart of a film due to strain-induced crystallinity and alignment of a majority of the polymer molecules in the direction of orientation) of the multi-layered polymer film, because the coPEN of the skin layers orients very little when stretched under the conditions used to orient the first optical layers 12.

Preferably, the polyesters of the first optical layers 12, the second optical layers 14, and the non-optical layers 18 are chosen to have similar rheological properties (e.g., melt viscosities) so that they can be co-extruded. Typically, the second optical layers 14 and the non-optical layers 18 have a glass transition temperature, $T_g$, that is either below or no greater than about 40° C. above the glass transition temperature of the first optical layers 12. Preferably, the glass transition temperature of the second optical layers 14 and the non-optical layers 18 is below the glass transition temperature of the first optical layers 12.

A polarizer may be made by combining a uniaxially-oriented first optical layer 12 with a second optical layer 14 having an isotropic index of refraction that is approximately equal to one of the in-plane indices of the oriented layer. Alternatively, both optical layers 12,14 are formed from birefringent polymers and are oriented in a multiple draw process so that the indices of refraction in a single in-plane direction are approximately equal. The interface between the two optical layers 12,14, in either case, forms a light reflection plane. Light polarized in a plane parallel to the direction in which the indices of refraction of the two layers are approximately equal will be substantially transmitted. Light polarized in a plane parallel to the direction in which the two layers have different indices will be at least partially reflected. The reflectivity can be increased by increasing the number of layers or by increasing the difference in the indices of refraction between the first and second layers 12, 14.

Typically, the highest reflectivity for a particular interface occurs at a wavelength corresponding to twice the combined optical thickness of the pair of optical layers 12, 14 which form the interface. The optical thickness of the two layers is $n_1 d_1 + n_2 d_2$ where $n_1$, $n_2$ are the indices of refraction of the two layers and $d_1$, $d_2$ are the thicknesses of the layers. The layers 12, 14 may each be a quarter wavelength thick or the layers 12, 14 may have different optical thicknesses, so long as the sum of the optical thicknesses is half of a wavelength (or a multiple thereof). A film having a plurality of layers may include layers with different optical thicknesses to increase the reflectivity of the film over a range of wavelengths. For example, a film may include pairs of layers which are individually tuned to achieve optimal reflection of light having particular wavelengths.

Alternatively, the first optical layers 12 may be biaxially-oriented by stretching in two different directions. The stretching of optical layers 12 in the two directions may result in a net symmetrical or asymmetrical stretch in the two chosen orthogonal axes.

One example of the formation of a mirror is the combination of a biaxially-oriented optical layer 22 with a second optical layer 24 having indices of refraction which differ from both the in-plane indices of the biaxially-oriented layer. The mirror operates by reflecting light having either polarization because of the index of refraction mismatch between the two optical layers 12, 14. Mirrors may also be made using a combination of uniaxially-oriented layers with in-plane indices of refraction which differ significantly. In another embodiment, the first optical layers 12 are not birefringent and a mirror is formed by combining first and second optical layers 12, 14 which have significantly different indices of refraction. Reflection occurs without orientation of the layers. There are other methods and combinations of layers that are known for producing both mirrors and polarizers and which may be used. Those particular combinations discussed above are merely exemplary.

The second optical layers 14 may be prepared with a variety of optical properties depending, at least in part, on the desired operation of the film 10. In one embodiment, the second optical layers 14 are made of a polymer material that does not appreciably optically orient when stretched under conditions which are used to orient the first optical layers 12. Such layers are particularly useful in the formation of reflective polarizing films, because they allow the formation of a stack 16 of layers by, for example, coextrusion, which can then be stretched to orient the first optical layers 12 while the second optical layers 14 remain relatively isotropic. Typically, the index of refraction of the second optical layers 14 is approximately equal to one of the indices of the oriented first optical layers 12 to allow transmission of light with a polarization in a plane parallel to the direction of the matched indices. Preferably, the two approximately equal indices of refraction differ by about 0.05 or less, and more preferably by about 0.02 or less, at 632.8 nm. In one embodiment, the index of refraction of the second optical layers 14 is approximately equal to the index of refraction of the first optical layers 12 prior to stretching.

In other embodiments, the second optical layers 14 are orientable. In some cases, the second optical layers 14 have one in-plane index of refraction that is substantially the same as the corresponding index of refraction of the first optical layers 12 after orientation of the two sets of layers 12, 14, while the other in-plane index of refraction is substantially different than that of the first optical layers 12. In other cases, particularly for mirror applications, both in-plane indices of refraction of the optical layers 12, 14 are substantially different after orientation.

Figure 2:
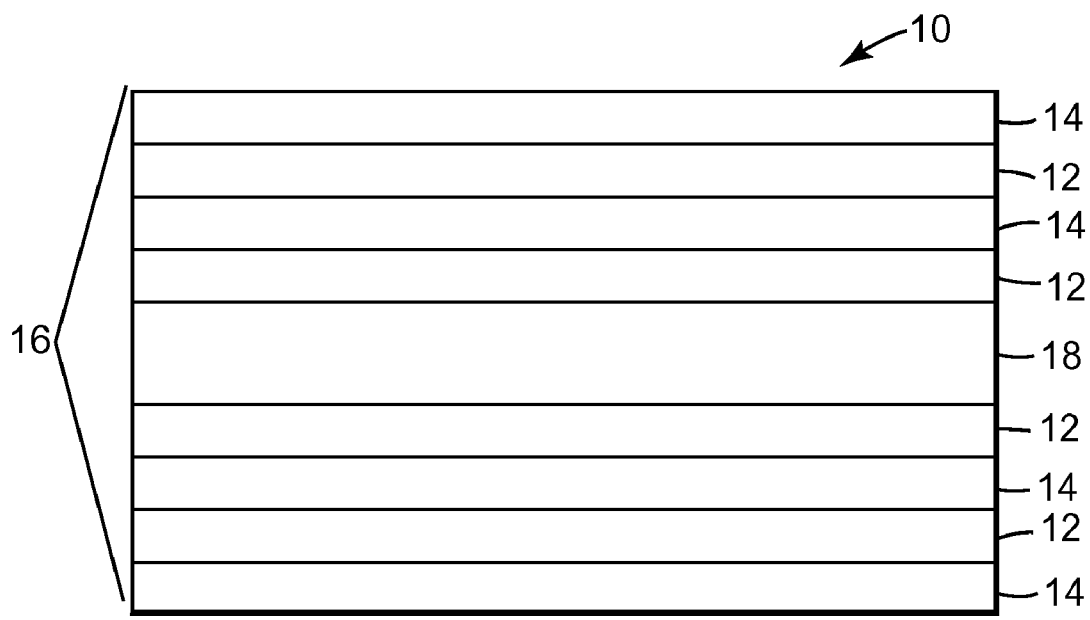
FIG. 2 is a cross-sectional view of another embodiment of a multilayered polymer film according to the present invention.

Referring again to FIGS. 1 and 2, one or more of the non-optical layers 18 may be formed as a skin layer over at least one surface of stack 16 as illustrated in FIG. 1, to, for example, protect the optical layers 12, 14 from physical damage during processing and/or afterwards. In addition, one or more of non-optical layers 18 may be formed within the stack 16 of layers, as illustrated in FIG. 2, to, for example, provide greater mechanical strength to the stack or to protect the stack during processing.

The non-optical layers 18 ideally do not significantly participate in the determination of optical properties of the multilayered polymer film 10, at least across the wavelength region of interest. The non-optical layers 18 are typically not birefringent or orientable but in some cases this may not be true. Typically, when the non-optical layers 18 are used as skin layers there will be at least some surface reflection. If the multilayered polymer film 10 is to be a polarizer, the non-optical layers preferably have an index of refraction which is relatively low. This decreases the amount of surface reflection. If the multilayered polymer film 10 is to be a mirror, the non-optical layers 18 preferably have an index of refraction which is high, to increase the reflection of light.

When the non-optical layers 18 are found within the stack 16, there will typically be at least some polarization or reflection of light by the non-optical layers 18 in combination with the optical layers 12, 14 adjacent to the non-optical layers 18. Typically, however, the non-optical layers 18 have a thickness which dictates that light reflected by the non-optical layers 18 within the stack 16 has a wavelength outside the region of interest, for example, in the infrared region for visible light polarizers or mirrors.

Various functional layers or coatings may be added to the films and optical devices of the present invention to alter or improve their physical or chemical properties, particularly along the surface of the film or device. Such layers or coatings may include, for example, slip agents, low adhesion backside materials, conductive layers, antistatic coatings or films, barrier layers, flame retardants, UV stabilizers, abrasion resistant materials, optical coatings, and/or substrates designed to improve the mechanical integrity or strength of the film or device.

Skin layers or coatings may also be added to impart desired barrier properties to the resulting film or device. Thus, for example, barrier films or coatings may be added as skin layers, or as a component in skin layers, to alter the transmissive properties of the film or device towards liquids, such as water or organic solvents, or gases, such as oxygen or carbon dioxide.

Skin layers or coatings may also be added to impart or improve abrasion resistance in the resulting article. Thus, for example, a skin layer comprising particles of silica embedded in a polymer matrix may be added to an optical film produced in accordance with the invention to impart abrasion resistance to the film, provided, of course, that such a layer does not unduly compromise the optical properties required for the application to which the film is directed.

Skin layers or coatings may also be added to impart or improve puncture and/or tear resistance in the resulting article. Factors to be considered in selecting a material for a tear resistant layer include percent elongation to break, Young's modulus, tear strength, adhesion to interior layers, percent transmittance and absorbance in an electromagnetic bandwidth of interest, optical clarity or haze, refractive indices as a function of frequency, texture and roughness, melt thermal stability, molecular weight distribution, melt rheology and coextrudability, miscibility and rate of inter-diffusion between materials in the skin and optical layers, viscoelastic response, relaxation and crystallization behavior under draw conditions, thermal stability at use temperatures, weatherability, ability to adhere to coatings and permeability to various gases and solvents. Puncture or tear resistant skin layers may be applied during the manufacturing process or later coated onto or laminated to the multilayered polymer film 10. Adhering these layers to the film during the manufacturing process, such as by a coextrusion process, provides the advantage that the film is protected during the manufacturing process. In some embodiments, one or more puncture or tear resistant layers may be provided within the film, either alone or in combination with a puncture or tear resistant skin layer.

The films and optical devices of the present invention may be given good slip properties by treating them with low friction coatings or slip agents, such as polymer beads coated onto the surface. Alternately, the morphology of the surfaces of these materials may be modified, as through manipulation of extrusion conditions, to impart a slippery surface to the film; methods by which surface morphology may be so modified are described in U.S. Pat. No. 5,759,467.

In some applications, as where the multilayered polymer films 10 of the present invention are to be used as a component in adhesive tapes, it may be desirable to treat the films with low adhesion backsize (LAB) coatings or films such as those based on urethane, silicone or fluorocarbon chemistry. Films treated in this manner will exhibit proper release properties towards pressure sensitive adhesives (PSAs), thereby enabling them to be treated with adhesive and wound into rolls. Adhesive tapes made in this manner can be used for decorative purposes or in any application where a diffusely reflective or transmissive surface on the tape is desirable.

The films and optical devices of the present invention may also be provided with one or more conductive layers. Such conductive layers may include metals such as silver, gold, copper, aluminum, chromium, nickel, tin, and titanium, metal alloys such as silver alloys, stainless steel, and inconel, and semiconductor metal oxides such as doped and undoped tin oxides, zinc oxide, and indium tin oxide (ITO).

The films and optical devices of the present invention may also be provided with antistatic coatings or films. Such coatings or films include, for example, $V_2O_5$ and salts of sulfonic acid polymers, carbon or other conductive metal layers.

The films and devices of the present invention may also be provided with one or more barrier films or coatings that alter the transmissive properties of the film towards certain liquids or gases. Thus, for example, the devices and films of the present invention may be provided with films or coatings that inhibit the transmission of water vapor, organic solvents, $O_2$, or $CO_2$ through the film. Barrier coatings may be particularly desirable in high humidity environments, where components of the film or device may be subject to distortion due to moisture permeation.

The films and optical devices of the present invention may also be treated with flame retardants, particularly when used in environments, such as on airplanes, that are subject to strict fire codes. Suitable flame retardants include aluminum trihydrate, antimony trioxide, antimony pentoxide, and flame retarding organophosphate compounds.

The films and optical devices of the present invention may also be provided with abrasion-resistant or hard coatings, which may be applied as a skin layer. These include acrylic hardcoats such as those available under the trade designations Acryloid A-11 and Paraloid K-120N from Rohm & Haas, Philadelphia, Pa.; urethane acrylates, such as those described in U.S. Pat. No. 4,249,011 and those available from Sartomer Corp., Westchester, Pa.; and urethane hardcoats obtained from the reaction of an aliphatic polyisocyanate (e.g., those available under the trade designation Desmodur N-3300 from Miles, Inc., Pittsburgh, Pa.) with a polyester (e.g., those available under the trade designation Tone Polyol 0305 from Union Carbide, Houston, Tex.).

The films and optical devices of the present invention may further be laminated to rigid or semi-rigid substrates, such as, for example, glass, metal, acrylic, polyester, and other polymer backings to provide structural rigidity, weatherability, or easier handling. For example, the multilayered polymer films 10 may be laminated to a thin acrylic or metal backing so that it can be stamped or otherwise formed and maintained in a desired shape. For some applications, such as when the film is applied to other breakable backings, an additional layer comprising PET film or puncture-tear resistant film may be used.

The films and optical devices of the present invention may also be provided with shatter resistant films and coatings. Films and coatings suitable for this purpose are described, for example, in publications EP 592284 and EP 591055, and are available commercially from 3M Company, St. Paul, Minn.

Various optical layers, materials, and devices may also be applied to, or used in conjunction with, the films and devices of the present invention for specific applications. These include, but are not limited to, magnetic or magneto-optic coatings or films; liquid crystal panels, such as those used in display panels and privacy windows; photographic emulsions; fabrics; prismatic films, such as linear Fresnel lenses; brightness enhancement films; holographic films or images; embossable films; anti-tamper films or coatings; IR transparent films for low emissivity applications; release films or release coated paper; and polarizers or mirrors.

Multiple additional layers on one or both major surfaces of the multilayered polymer film 10 are contemplated, and can be any combination of the aforementioned coatings or films. For example, when an adhesive is applied to the multilayered polymer film 10, the adhesive may contain a white pigment such as titanium dioxide to increase the overall reflectivity, or it may be optically transparent to allow the reflectivity of the substrate to add to the reflectivity of the multilayered polymer film 10.

In order to improve roll formation and convertibility of the film, the multilayered polymer films 10 of the present invention may also include a slip agent that is incorporated into the film or added as a separate coating. In most applications, slip agents are added to only one side of the film, ideally the side facing the rigid substrate in order to minimize haze.

The films and other optical devices made in accordance with the invention may also include one or more anti-reflective layers or coatings, such as, for example, conventional vacuum coated dielectric metal oxide or metal/metal oxide optical films, silica sol gel coatings, and coated or coextruded anti-reflective layers such as those derived from low index fluoropolymers such as THV, an extrudable fluoropolymer available from 3M Company (St. Paul, Minn.). Such layers or coatings, which may or may not be polarization sensitive, serve to increase transmission and to reduce reflective glare, and may be imparted to the films and optical devices of the present invention through appropriate surface treatment, such as coating or sputter etching.

The films and other optical devices made in accordance with the invention may be provided with a film or coating which imparts anti-fogging properties. In some cases, an anti-reflection layer as described above will serve the dual purpose of imparting both anti-reflection and anti-fogging properties to the film or device. Various anti-fogging agents are known to the art. Typically, however, these materials include substances, such as fatty acid esters, which impart hydrophobic properties to the film surface and which promote the formation of a continuous, less opaque film of water.

Coatings which reduce the tendency for surfaces to "fog" have been reported by several inventors. For example, U.S. Pat. No. 3,212,909 to Leigh discloses the use of ammonium soap, such as alkyl ammonium carboxylates in admixture with a surface active agent which is a sulfated or sulfonated fatty material, to produce a anti-fogging composition. U.S. Pat. No. 3,075,228 to Elias discloses the use of salts of sulfated alkyl aryloxypolyalkoxy alcohol, as well as alkylbenzene sulfonates, to produce an anti-fogging article useful in cleaning and imparting anti-fogging properties to various surfaces. U.S. Pat. No. 3,819,522 to Zmoda, discloses the use of surfactant combinations comprising derivatives of decyne diol as well as surfactant mixtures which include ethoxylated alkyl sulfates in an anti-fogging window cleaner surfactant mixture. Japanese Patent Kokai No. Hei 6[1994]41,335 discloses a clouding and drip preventive composition comprising colloidal alumina, colloidal silica and an anionic surfactant. U.S. Pat. No. 4,478,909 (Taniguchi et al) discloses a cured anti-fogging coating film which comprises polyvinyl alcohol, a finely divided silica, and an organic silicon compound, the carbon/silicon weight ratio apparently being important to the film's reported anti-fogging properties. Various surfactants, include fluorine-containing surfactants, may be used to improve the surface smoothness of the coating. Other anti-fog coatings incorporating surfactants are described in U.S. Pat. Nos. 2,803,552; 3,022,178; and 3,897,356. PCT 96/18,691 (Scholtz et al) discloses means by which coatings may impart both anti-fog and anti-reflective properties.

The films and optical devices of the present invention may be protected from UV radiation through the use of UV stabilized films or coatings. Suitable UV stabilized films and coatings include those which incorporate benzotriazoles or hindered amine light stabilizers (HALS) such as those available under the trade designation Tinuvin 292 from Ciba Geigy Corp., Hawthorne, N.Y. Other suitable UV stabilized films and coatings include those which contain benzophenones or diphenyl acrylates, available commercially from BASF Corp., Parsippany, N.J. Such films or coatings may be particularly desirable when the films and optical devices of the present invention are used in outdoor applications or in luminaires where the source emits significant amount of light in the UV region of the spectrum.

The films and optical devices of the present invention may be treated with inks, dyes, or pigments to alter their appearance or to customize them for specific applications. Thus, for example, the films may be treated with inks or other printed indicia such as those used to display product identification, advertisements, warnings, decoration, or other information. Various techniques may be used to print on the film, such as screen printing, letterpress, offset, flexographic printing, stipple printing, laser printing, and so forth, and various types of ink can be used, including one and two component inks, oxidatively drying and UV-drying inks, dissolved inks, dispersed inks, and 100% ink systems. In addition, dyes or pigments may be blended into a polymer either before or after formation of layers using the polymer.

The appearance of the multilayered polymer film 10 may also be altered by coloring the film, such as by laminating a dyed film to the multilayered polymer film, applying a pigmented coating to the surface of the film, or including a pigment in one or more of the materials used to make the film.

Both visible and near IR dyes and pigments are contemplated in the present invention, and include, for example, optical brighteners such as dyes that absorb in the UV and fluoresce in the visible region of the color spectrum. Other additional layers that may be added to alter the appearance of the optical film include, for example, opacifying (black) layers, diffusing layers, holographic images or holographic diffusers, and metal layers. Each of these may be applied directly to one or both surfaces of film, or may be a component of a second film or foil construction that is laminated to the film. Alternately, some components such as opacifying or diffusing agents, or colored pigments, may be included in an adhesive layer which is used to laminate the film to another surface.

The films and devices of the present invention may also be provided with metal coatings. Thus, for example, a metallic layer may be applied directly to the optical film by pyrolysis, powder coating, vapor deposition, cathode sputtering, ion plating, and the like. Metal foils or rigid metal plates may also be laminated to the optical film, or separate polymeric films or glass or plastic sheets may be first metallized using the aforementioned techniques and then laminated to the films and devices of the present invention.

A brief description of one method for forming multilayer polymer films is described. A fuller description of the process conditions and considerations is found in U.S. patent application Ser. No. 09/006,288 entitled "Process for Making Multilayer Optical Film." The multilayer polymer films are formed by extrusion of polymers to be used in the first and second optical layers, as well as the non-optical layers. Extrusion conditions are chosen to adequately feed, melt, mix and pump the polymer resin feed streams in a continuous and stable manner. Final melt stream temperatures are chosen to be within a range which reduces freezing, crystallization or unduly high pressure drops at the low end of the range and which reduces degradation at the high end of the range. The entire melt stream processing of more than one polymer, up to and including film casting on a chill roll, is often referred to as co-extrusion.

Following extrusion, each melt stream is conveyed through a neck tube into a gear pump used to regulate the continuous and uniform rate of polymer flow. A static mixing unit may be placed at the end of the neck tube to carry the polymer melt stream from the gear pump into a multilayer feedblock with uniform melt stream temperature. The entire melt stream is typically heated as uniformly as possible to enhance both uniform flow of the melt stream and reduce degradation during melt processing.

Multilayer feedblocks divide each of two or more polymer melt streams into many layers, interleave these layers, and combine the many layers into a single multilayer stream. The layers from any given melt stream are created by sequentially bleeding off part of the stream from a main flow channel into side channel tubes which lead to layer slots in the feed block manifold. The layer flow is often controlled by choices made in machinery, as well as the shape and physical dimensions of the individual side channel tubes and layer slots.

The side channel tubes and layer slots of the two or more melt streams are often interleaved to, for example, form alternating layers. The feedblock's downstream-side manifold is often shaped to compress and uniformly spread the layers of the combined multilayer stack transversely. Thick, non-optical layers, known as protective boundary layers (PBLs), may be fed near the manifold walls using the melt streams of the optical multilayer stack, or by a separate melt stream. As described above, these non-optical layers may be used to protect the thinner optical layers from the effects of wall stress and possible resulting flow instabilities.

The multilayer stack exiting the feedblock manifold may then enter a final shaping unit such as a die. Alternatively, the stream may be split, preferably normal to the layers in the stack, to form two or more multilayer streams that may be recombined by stacking. The stream may also be split at an angle other than normal to the layers. A flow channeling system that splits and stacks the streams is called a multiplier. The width of the split streams (i.e., the sum of the thicknesses of the individual layers) can be equal or unequal. The multiplier ratio is defined as the ratio of the wider to narrower stream widths. Unequal streams widths (i.e., multiplier ratios greater than unity) can be useful in creating layer thickness gradients. In the case of unequal stream widths, the multiplier may spread the narrower stream and/or compress the wider stream transversely to the thickness and flow directions to ensure matching layer widths upon stacking.

Prior to multiplication, additional non-optical layers can be added to the multilayer stack. These non-optical layers may perform as PBLs within the multiplier. After multiplication and stacking, some of these layers may form internal boundary layers between optical layers, while others form skin layers.

After multiplication, the web is directed to the final shaping unit. The web is then cast onto a chill roll, sometimes also referred to as a casting wheel or casting drum. This casting is often assisted by electrostatic pinning, the details of which are well-known in the art of polymer film manufacture. The web may be cast to a uniform thickness across the web or a deliberate profiling of the web thickness may be induced using die lip controls.

The multilayer web is then drawn to produce the final multilayer optical film. In one exemplary method for making a multilayer optical polarizer, a single drawing step is used. This process may be performed in a tenter or a length orienter. Typical tenters draw transversely (TD) to the web path, although certain tenters are equipped with mechanisms to draw or relax (shrink) the film dimensionally in the web path or machine direction (MD). Thus, in this exemplary method, a film is drawn in one in-plane direction. The second in-plane dimension is either held constant as in a conventional tenter, or is allowed to neck in to a smaller width as in a length orienter. Such necking in may be substantial and increase with draw ratio.

In one exemplary method for making a multilayer mirror, a two step drawing process is used to orient the birefringent material in both in-plane directions. The draw processes may be any combination of the single step processes described that allow drawing in two in-plane directions. In addition, a tenter that allows drawing along MD, e.g. a biaxial tenter which can draw in two directions sequentially or simultaneously, may be used. In this latter case, a single biaxial draw process may be used.

In still another method for making a multilayer polarizer, a multiple drawing process is used that exploits the different behavior of the various materials to the individual drawing steps to make the different layers comprising the different materials within a single coextruded multilayer film possess different degrees and types of orientation relative to each other. Mirrors can also be formed in this manner.

The intrinsic viscosity of the polyesters used in these layers and films is related to the molecular weight (in the absence of branching monomers) of the polymer. Typically, the polyesters have an intrinsic viscosity of greater than about 0.4 dL/g. Preferably, the intrinsic viscosity is between about 0.4 to 0.7 dL/g. Intrinsic viscosity, for purposes of this disclosure, is measured in a 60/40 wt. % phenol/o-dichlorobenzene solvent at 30° C. unless otherwise indicated.

The following examples demonstrate the manufacture and uses of multilayered polymer films of the invention. It is to be understood that these examples are merely illustrative and are in no way to be interpreted as limiting the scope of the invention.

EXAMPLES

Monomers, catalysts, and stabilizers utilized in creating polymers for these examples are commercially available from the following suppliers: dimethyl naphthalene dicarboxylate and terephthalic acid from Amoco (Decatur, Ala.), dimethyl terephthalate from Hoechst Celanese (Dallas, Tex.), dimethyl isophthalate and dimethyl tertiary-butyl isophthalate from Morflex Inc. (Greensboro, N.C.), ethylene glycol from Union Carbide (Charleston, W. Va.), 1,6-hexanediol from BASF (Charlotte, N.C.), sebacic acid from Union Camp (Dover, Ohio), antimony triacetate from Elf Atochem (Philadelphia, Pa.), cobalt acetate and manganese acetate from Hall Chemical (Wickliffe, Ohio), triethyl phosphonoacetate from Albright & Wilson (Glen Allen, Va.), dimethyl cyclohexane dicarboxylate from Eastman Chemical Co. (Kingsport, Tenn.), and triethylamine from Air Products (Phillipsburg, N.J.).

In each of the examples described below, an 836 layer film is formed. The 836 optical layer construction includes four multilayer optical stacks of graded layer thicknesses as obtained by the double multiplication of a 209 layer construction from a multilayer feed block. The optical layers account for approximately 50 percent of the thickness of the construction. Each of the stacks is separated by one of three non-optical internal protective boundary layers, each accounting for about 2% of the total thickness. Finally, each side of the film possesses an outer non-optical skin layer, each accounting for approximately 22% of the thickness.

A "gain tester" was used to test several of the films in the Examples. The "gain tester" can be fabricated using a spot photometer and a suitable backlight with a polarizer placed between the two so that only one polarization of light from the backlight is measured by the photometer. Suitable spot photometers include the Minolta LS-100 and LS-110 (Ramsey, N.J.). The absolute value of a measured gain on the backlight used and on the orientation of the sample on the backlight, as well as the size of the sample. The backlight used in the Examples was obtained from Landmark and the polarizer was a high contrast display polarizer which was oriented so that the pass axis of the polarizer was aligned with the long axis of the backlight. The sample was inserted into the tester so that the pass axis of the sample was aligned with the pass axis of the high contrast polarizer. The sample was made large enough to cover the entire backlight.

Comparative Example

Polarizing Film with PEN/coPEN (70/0/30) Layers.

As a comparative example, a multilayer reflective polarizer film was constructed with first optical layers created from polyethylene naphthalate and second optical layers created from co(polyethylene naphthalate) with carboxylate subunits derived from 70 mol % dimethyl naphthalene dicarboxylate and 30 mol % dimethyl isophthalate, and glycol subunits derived from 100 mol % ethylene glycol.

The polyethylene naphthalate used to form the first optical layers was synthesized in a batch reactor with the following raw material charge: 136 kg dimethyl naphthalene dicarboxylate, 73 kg ethylene glycol, 27 g manganese acetate, 27 g cobalt acetate, and 48 g antimony triacetate. Under pressure of 2 atm ($2 \times 10^5$ N/m$^2$), this mixture was heated to 254° C. while removing methanol (a transesterification reaction by-product). After 35 kg of methanol was removed, 49 g of triethyl phosphonoacetate was charged to the reactor and than the pressure was gradually reduced to 1 torr while heating to 290° C. The condensation reaction by-product, ethylene glycol, was continuously removed until a polymer with an intrinsic viscosity of 0.48 dL/g, as measured in 60/40 wt. % phenol/o-dichlorobenzene, was produced.

The co(polyethylene naphthalate) used to form the second optical layers was synthesized in a batch reactor with the following raw material charge: 109 kg dimethyl naphthalene dicarboxylate, 37 kg dimethyl isophthalate, 79 kg ethylene glycol, 29 g manganese acetate, 29 g cobalt acetate, and 58 g antimony triacetate. Under pressure of 2 atm ($2 \times 10^5$ N/m$^2$), this mixture was heated to 254° C. while removing methanol. After 41 kg of methanol was removed, 52 g of triethyl phosphonoacetate was charged to the reactor and than the pressure was gradually reduced to 1 torr while heating to 290° C. The condensation reaction by-product, ethylene glycol, was continuously stripped until a polymer with an intrinsic viscosity of 0.57 dL/g, as measured in 60/40 wt. % phenol/o-dichlorobenzene, was produced.

The above described PEN and coPEN were then coextruded through multilayer melt manifolds to create a multilayer film with 836 alternating first and second optical layers. This multilayer reflective film also contains internal protective layers and external protective layers made of the same co(polyethylene naphthalate) as the second optical layers. These protective layers are introduced through additional melt ports. This cast film was heated in an oven charged with hot air set at 150° C. for about one minute and then uniaxially oriented at a 6:1 draw to produce a reflective polarizer film of approximately 125 µm thickness.

When the described multilayer reflective film was placed within a "gain tester", as described above, the brightness increased by 58% which correlates to a "gain" of 1.58. Increases in brightness are measured as gain, which is the ratio of the brightness of a tester with the polarizing film to the brightness of the tester without the polarizing film.

A second film was constructed and processed as above, except that this second film was uniaxially oriented at a 7:1 draw. The resulting birefringence of the second film was estimated to be about 0.24 at 632.8 nm. The average gain of the second film was estimated to be about 1.62.

A peel strength test was performed. Samples of the second film were cut in 2.54 cm strips at 45° with respect to the reflection and transmission axes (i.e., in-plane axes) of the film. The multilayer optical film was adhered to a substrate and then, using an Instrumentors, Inc. slip/peel tester (Strongsville, Ohio), the layers of the film were peeled away at 2.54 cm/second at 25° C., 50% relative humidity, and 90° peel angle. The error in the test was estimated to be about ±8×10³ dynes/cm. For this second film, the resistance to delamination between the two set of optical layers was about $1.2 \times 10^4$ dynes/cm, which is relatively low.

A third multilayer reflective polarizer film was constructed and processed in a manner similar to the first two films except that the film was preheated in a tenter with hot air charged at a temperature of about 160° C. and then drawn with the air charged at about 150° C. The in-plane birefringence of this film was estimated to be about 0.17 for 632.8 nm light. The average gain was estimated to be about 1.53. The resistance to delamination was about $6.2 \times 10^4$ dynes/cm.

Example 1

Polarizing Film with coPEN (90/10/0)/coPEN (55/0/45) Layers.

A multilayer reflective polarizer film may be constructed with first optical layers created from a co(polyethylene naphthalate) with carboxylate subunits derived from 90 mol % dimethyl naphthalene dicarboxylate and 10 mol % dimethyl terephthalate, and glycol subunits derived from 100 mol % ethylene glycol subunits, and second optical layers created from a co(polyethylene naphthalate) with carboxylate subunits derived from 55 mol % dimethyl naphthalene dicarboxylate and 45 mol % dimethyl isophthalate, and glycol subunits derived from 99.8 mol % ethylene glycol and 0.2 mol % trimethylol propane.

The co(polyethylene naphthalate) used to form the first optical layers is synthesized in a batch reactor with the following raw material charge: 126 kg dimethyl naphthalene dicarboxylate, 11 kg dimethyl terephthalate, 75 kg ethylene glycol, 27 g manganese acetate, 27 g cobalt acetate, and 48 g antimony triacetate. Under pressure of 2 atm ($2 \times 10^5$ N/m²), this mixture is heated to 254° C. while removing methanol. After 36 kg of methanol is removed, 49 g of triethyl phosphonoacetate is charged to the reactor and than the pressure is gradually reduced to 1 torr while heating to 290° C. The condensation reaction by-product, ethylene glycol, is continuously removed until a polymer with an intrinsic viscosity of 0.50 dL/g, as measured in 60/40 wt. % phenol/o-dichlorobenzene, is produced.

The co(polyethylene naphthalate) used to form the second optical layers is synthesized in a batch reactor with the following raw material charge: 83 kg dimethyl naphthalene dicarboxylate, 54 kg dimethyl isophthalate, 79 kg ethylene glycol, 313 g trimethylol propane, 27 grams manganese acetate, 27 grams cobalt acetate, and 48 g antimony triacetate. Under pressure of 2 atm ($2 \times 10^5$ N/m²), this mixture is heated to 254° C. while removing methanol. After 39.6 kg of methanol is removed, 49 g of triethyl phosphonoacetate is charged to the reactor and than the pressure is gradually reduced to 1 torr while heating to 290° C. The condensation reaction byproduct, ethylene glycol, is continuously stripped until a polymer with an intrinsic viscosity of 0.60 dL/g, as measured in 60/40 wt. % phenol/o-dichlorobenzene, is produced.

The above described coPEN's are then coextruded through a multilayer melt manifold to create a multilayer film with 836 alternating first and second optical layers. This particular multilayer reflective film also contains internal and external protective layers made of the same co(polyethylene naphthalate) as the second optical layers. The cast film is heated in an oven charged with hot air set at 145° C. for about one minute and then uniaxially oriented at a 6:1 draw to produce a reflective polarizer of approximately 125 µm thickness.

Example 2

Polarizing Film with coPEN (85/15/0)/coPEN (50/0/50) Layers.

A multilayer reflective polarizer film was constructed with first optical layers created from a co(polyethylene naphthalate) with carboxylate subunits derived from 85 mol % dimethyl naphthalene dicarboxylate and 15 mol % dimethyl terephthalate, and glycol subunits derived from 100 mol % ethylene glycol, and second optical layers created from a co(polyethylene naphthalate) with carboxylate subunits derived from 50 mol % dimethyl naphthalene dicarboxylate and 50 mol % dimethyl isophthalate, and glycol subunits derived from 100 mol % ethylene glycol.

The co(polyethylene naphthalate) used to form the first optical layers was synthesized in a batch reactor with the following raw material charge: 123 kg dimethyl naphthalene dicarboxylate, 17 kg dimethyl terephthalate, 76 kg ethylene glycol, 27 g manganese acetate, 27 g cobalt acetate, and 48 g antimony triacetate. Under pressure of 2 atm ($2 \times 10^5$ N/m²), this mixture was heated to 254° C. while removing methanol. After 36 kg of methanol was removed, 49 g of triethyl phosphonoacetate was charged to the reactor and than the pressure was gradually reduced to 1 torr while heating to 290° C. The condensation reaction by-product, ethylene glycol, was continuously removed until a polymer with an intrinsic viscosity of 0.51 dL/g, as measured in 60/40 wt. % phenol/o-dichlorobenzene, was produced.

The co(polyethylene naphthalate) used to form the second optical layers was synthesized in a batch reactor with the following raw material charge: 77 kg dimethyl naphthalene dicarboxylate, 61 kg dimethyl isophthalate, 82 kg ethylene glycol, 27 grams manganese acetate, 27 grams cobalt acetate, and 48 g antimony triacetate. Under pressure of 2 atm ($2 \times 10^5$ N/m²), this mixture was heated to 254° C. while removing methanol. After 39.6 kg of methanol was removed, 49 g of triethyl phosphonoacetate was charged to the reactor and than the pressure was gradually reduced to 1 torr while heating to 290° C. The condensation reaction by-product, ethylene glycol, was continuously stripped until a polymer with an intrinsic viscosity of 0.60 dL/g, as measured in 60/40 wt. % phenol/o-dichlorobenzene, was produced.

The above described coPEN's were then coextruded through a multilayer melt manifold to create a multilayer film with 836 alternating first and second optical layers. This particular multilayer reflective film also contained internal and external protective layers made of the same co(polyethylene naphthalate) as the second optical layers. The cast film was heated in an oven charged with hot air set at 135° C. for about one minute and then uniaxially oriented at a 6:1 draw to produce a reflective polarizer of approximately 125 µm thickness. The resulting in-plane birefringence was estimated to be about 0.17 for 632.8 nm light. The resistance to interlayer delamination was about $5.9 \times 10^4$ dynes/cm.

When the described multilayer reflective film was placed within a "gain tester", as described above, the brightness increased by 58% which correlates to a "gain" of 1.58. Increases in brightness are measured as gain, which is the ratio of the brightness of a tester with the polarizing film to the brightness of the tester without the polarizing film.

A second film was formed in the same manner except that the second film was drawn in hot air charged to 129° C. The resulting in-plane birefringence was estimated to be about 0.185. The measured gain was 1.58 and the resistance to interlayer delamination was about $4.5 \times 10^4$ dynes/cm.

Example 3

Polarizing Film with coPEN (88/12/0)/coPEN (55/45/0) Layers.

A multilayer reflective polarizer film was constructed with first optical layers created from a co(polyethylene naphthalate) with carboxylate subunits derived from 88 mol % dimethyl naphthalene dicarboxylate and 12 mol % dimethyl terephthalate, and glycol subunits derived from 100 mol % ethylene glycol, and second optical layers created from a co(polyethylene naphthalate) with carboxylate subunits derived from 55 mol % dimethyl naphthalene dicarboxylate and 45 mol % dimethyl terephthalate, and glycol subunits derived from 96.8 mol % ethylene glycol, 3.0 mol % hexanediol, and 0.2 mol % trimethylol propane.

The co(polyethylene naphthalate) used to form the first optical layers was created as a blend of two polymers: a PET (8 wt. %) and a coPEN (92 wt. %). The PET used in the blend was synthesized in a batch reactor with the following raw material charge: 138 kg dimethyl terephthalate, 93 kg ethylene glycol, 27 g zinc acetate, 27 g cobalt acetate, and 48 g antimony triacetate. Under pressure of 2 atm ($2 \times 10^5$ N/m$^2$), this mixture was heated to 254° C. while removing the transesterification reaction byproduct, methanol. After 45 kg of methanol was removed 52 g of triethyl phosphonoacetate was charged to the reactor and then the pressure was gradually reduced to 1 torr while heating to 290° C. The condensation reaction byproduct, ethylene glycol, was continuously removed until a polymer with an intrinsic viscosity of 0.60, as measured in 60/40 wt. % phenol/o-dichlorobenzene, was produced.

The coPEN used in the blend to form the first optical layers had carboxylate subunits that were derived from 97 mol % dimethyl naphthalene dicarboxylate and 3 mol % dimethyl terephthalate and glycol subunits derived from 100 mol % ethylene glycol. The coPEN was synthesized in a batch reactor with the following raw material charge: 135 kg dimethyl naphthalene dicarboxylate, 3.2 kg dimethyl terephthalate, 75 kg ethylene glycol, 27 g manganese acetate, 27 g cobalt acetate, and 48 g antimony triacetate. Under pressure of 2 atm ($2 \times 10^5$ N/m$^2$), this mixture was heated to 254° C. while removing methanol. After 37 kg of methanol was removed, 49 g of triethyl phosphonoacetate was charged to the reactor and than the pressure was gradually reduced to 1 torr while heating to 290° C. The condensation reaction by-product, ethylene glycol, was continuously removed until a polymer with an intrinsic viscosity of 0.50 dL/g, as measured in 60/40 wt. % phenol/o-dichlorobenzene, was produced.

The co(polyethylene naphthalate) used to form the second optical layers was synthesized in a batch reactor with the following raw material charge: 88.5 kg dimethyl naphthalene dicarboxylate, 57.5 kg dimethyl terephthalate, 81 kg ethylene glycol, 4.7 kg hexane diol, 15 grams manganese acetate, 22 grams cobalt acetate, 15 g zinc acetate, 239 g trimethylol propane, and 51 g antimony triacetate. Under pressure of 2 atm ($2 \times 10^5$ N/m$^2$), this mixture was heated to 254° C. while removing methanol. After 39.6 kg of methanol was removed, 47 g of triethyl phosphonoacetate was charged to the reactor and than the pressure was gradually reduced to 1 torr while heating to 290° C. The condensation reaction by-product, ethylene glycol, was continuously stripped until a polymer with an intrinsic viscosity of 0.56 dL/g, as measured in 60/40 wt. % phenol/o-dichlorobenzene, was produced.

The above described coPEN's were then coextruded through a multilayer melt manifold to create a multilayer film with 836 alternating first and second optical layers. This particular multilayer reflective film also contained internal and external protective layers made of the same co(polyethylene naphthalate) as the second optical layers. The cast film was heated in an oven charged with hot air set at 140° C. for about one minute and then uniaxially oriented at a 6:1 draw to produce a reflective polarizer of approximately 125 µm thickness.

When the described multilayer reflective film was placed within a "gain tester", as described above, the brightness increased by 58% which correlates to a "gain" of 1.58. Increases in brightness are measured as gain, which is the ratio of the brightness of a tester with the polarizing film to the brightness of the tester without the polarizing film.

Interlayer adhesion was measured to be about $9.5 \times 10^4$ dynes/cm using the 90 degree tape peel test.

Example 4

Polarizing Film with coPEN (85/15/0)/coPEN (55/45/0) Layers.

A multilayer reflective polarizer film was constructed with first optical layers created from a co(polyethylene naphthalate) with carboxylate subunits derived from 85 mol % dimethyl naphthalene dicarboxylate and 15 mol % dimethyl terephthalate, and glycol subunits derived from 100 mol % ethylene glycol subunits, and second optical layers created from a co(polyethylene naphthalate) with carboxylate subunits derived from 55 mol % dimethyl naphthalene dicarboxylate and 45 mol % dimethyl terephthalate and glycol subunits derived from 96.8 mol % ethylene glycol, 3.0 mol % hexane diol, and 0.2 mol % trimethylol propane.

The co(polyethylene naphthalate) used to form the first optical layers was synthesized as in Example 2.

The co(polyethylene naphthalate) used to form the second optical layers was synthesized as in Example 3.

The above described coPEN's were then coextruded through a multilayer melt manifold to create a multilayer film with 836 alternating first and second optical layers. This particular multilayer reflective film also contained internal and external protective layers made of the same co(polyethylene naphthalate) as the second optical layers. The cast film was heated in an oven charged with hot air set at 135° C. for about one minute and then uniaxially oriented at a 6:1 draw to produce a reflective polarizer of approximately 125 µm thickness.

When the described multilayer reflective film was placed within a "gain tester", as described above, the brightness increased by 58% which correlates to a "gain" of 1.58. Increases in brightness are measured as gain, which is the ratio of the brightness of a tester with the polarizing film to the brightness of the tester without the polarizing film.

Example 5

Polarizing Film with coPEN (85/15/0)/coPEN (50/50/0) Layers.

A multilayer reflective polarizer film was constructed with first optical layers created from a co(polyethylene naphthalate) with carboxylate subunits derived from 85 mol % dimethyl naphthalene dicarboxylate and 15 mol % dimethyl terephthalate and glycol subunits derived from 100 mol % ethylene glycol, and second optical layers created from a co(polyethylene naphthalate) with carboxylate subunits derived from 50 mol % dimethyl naphthalene dicarboxylate and 50 mol % dimethyl terephthalate and glycol subunits derived from 96.8 mol % ethylene glycol, 3.0 mol % hexane diol, and 0.2 mol % trimethylol propane.

The co(polyethylene naphthalate) used to form the first optical layers was synthesized as in Example 2.

The co(polyethylene naphthalate) used to form the second optical layers was synthesized in a batch reactor with the following raw material charge: 81.4 kg dimethyl naphthalene dicarboxylate, 64.5 kg dimethyl terephthalate, 82 kg ethylene glycol, 4.7 kg hexane diol, 15 g manganese acetate, 22 g cobalt acetate, 15 g zinc acetate, 239 g trimethylol propane, and 48 g antimony triacetate. Under pressure of 2 atm ($2 \times 10^5$ N/m$^2$), this mixture was heated to 254° C. while removing methanol. After 44 kg of methanol was removed, 47 g of triethyl phosphonoacetate was charged to the reactor and than the pressure was gradually reduced to 1 torr while heating to 290° C. The condensation reaction by-product, ethylene glycol, was continuously stripped until a polymer with an intrinsic viscosity of 0.60 dL/g, as measured in 60/40 wt. % phenol/o-dichlorobenzene, was produced.

The above described coPEN's were then coextruded through a multilayer melt manifold to create a multilayer film with 836 alternating first and second optical layers. This particular multilayer reflective film also contained internal and external protective layers made of the same co(polyethylene naphthalate) as the second optical layers. The cast film was heated in an oven charged with hot air set at 135° C. for about one minute and then uniaxially oriented at a 6:1 draw to produce a reflective polarizer of approximately 125 µm thickness.

When the described multilayer reflective film was placed within a "gain tester", as described above, the brightness increased by 58% which correlates to a "gain" of 1.58. Increases in brightness are measured as gain, which is the ratio of the brightness of a tester with the polarizing film to the brightness of the tester without the polarizing film.

Example 6

Polarizing Film with Second Optical Layers Derived from Dimethyl Cyclohexane Dicarboxylate.

A multilayer reflective polarizer film may be constructed with first optical layers created from a copolyester having carboxylate subunits derived from 100 mol % dimethyl terephthalate and glycol subunits derived from 90 mol % 1,4-butanediol and 10 mol % ethylene glycol. The second optical layers are made from a copolyester which has carboxylate subunits derived from 50 mol % cyclohexane dicarboxylic acid and 50 mol % terephthalic acid and glycol subunits derived from 99.8 mol % ethylene glycol, and 0.2 mol % trimethylol propane.

The poly(butylene terephthalate) used to form the first optical layers is synthesized in a batch reactor with the following raw material charge: 127 kg dimethyl terephthalate, 77 kg 1,4-butanediol, 9 kg ethylene glycol, and 11 g tetrabutyl titanate. Under pressure of 2 atm ($2 \times 10^5$ N/m$^2$), this mixture is heated to 254° C. while removing the transesterification reaction by-product, methanol. After removing 41 kg of methanol, the reactor pressure is reduced to atmospheric pressure and excess 1,4-butanediol is removed. Another 22 grams of tetrabutyl titanate is then charged to the reactor and the pressure is further reduced to 1 torr while heating to 270° C. The polycondensation by-product, 1,4-butanediol, is continuously stripped until a polymer with an intrinsic viscosity of 0.85 dL/g, as measured in 60/40 wt. % phenol/o-dichlorobenzene, is produced.

The copolyester used to form the second optical layers is synthesized in a batch reactor with the following raw material charge: 58.6 terephthalic acid 59.5 kg cyclohexane dicarboxylic acid, 87.7 kg ethylene glycol, 300 g triethyl amine, 275 g trimethylol propane, and 82 g antimony triacetate. Under pressure of 2 atm ($2 \times 10^5$ N/m$^2$), this mixture is heated to 254° C. while removing the transesterification reaction by-product, water. After 25.5 kg of water is removed, the pressure is gradually reduced to 1 torr while heating to 290° C. The condensation reaction by-product, ethylene glycol, is continuously stripped until a polymer with an intrinsic viscosity of 1.1 dL/g, as measured in 60/40 wt. % phenol/o-dichlorobenzene, is produced.

The above-described copolyesters are then coextruded through a multilayer melt manifold to create a multilayer film with 836 alternating first and second optical layers. This particular multilayer reflective film also contains internal protective layers and external protective layers made from of the same copolyester as the second optical layers. The cast film is heated in an oven charged with hot air set at 65° C. for about one minute and then uniaxially oriented at a 6:1 draw to produce a reflective polarizer of approximately 125 µm thickness.

Example 7

Mirror Film with Second Optical Layers Derived from Dimethyl Cyclohexane Dicarboxylate and Tertiary Isophthalate.

A multilayer reflective mirror film may be constructed with first optical layers created from coPEN having carboxylate subunits derived from 90 mol % dimethyl naphthalene dicarboxylate and 10 mol % dimethyl terephthalate and glycol subunits derived 100 mol % ethylene glycol. The second optical layers are made from a copolyester which has carboxylate subunits derived from 85 mol % cyclohexane dicarboxylic acid and 15 mol % dimethyl tertiary-butyl isophthalate and glycol subunits derived from 99.7 mol % ethylene glycol, and 0.3 mol % trimethylol propane.

The coPEN used to form the first optical layers is synthesized as in Example 1.

The copolyester used to form the second optical layers is synthesized in a batch reactor with the following raw material charge: 25.5 kg dimethyl tertiary-butyl isophthalate, 112 kg cyclohexane dicarboxylic acid, 88 kg ethylene glycol, 409 g trimethylol propane, 34 g copper acetate, 27 g manganese acetate, and 82 g antimony triacetate. Under pressure of 2 atm ($2 \times 10^5$ N/m$^2$), this mixture is heated to 254° C. while removing the transesterification reaction by-product, methanol. After 43 kg of methanol is removed, the pressure is gradually reduced to 1 torr while heating to 290° C. The condensation reaction by-product, ethylene glycol, is continuously stripped until a polymer with an intrinsic viscosity of 1.2 dL/g, as measured in 60/40 wt. % phenol/o-dichlorobenzene, is produced.

The above-described copolyesters are then coextruded through a multilayer melt manifold to create a multilayer film with 836 alternating first and second optical layers. This particular multilayer reflective film also contains internal protective layers and external protective layers made from of the same copolyester as the second optical layers. This cast film is biaxially oriented. First, the film is heated in an oven charged with hot air set at 120° C. for about one minute and then oriented at a 3.6:1 draw. Then the film is heated in an oven charged with hot air set at 135° C. for about one minute and then oriented in a transverse direction at a 4.0:1 draw.

Example 8

Polarizing Film with PEN Optical Layers, Low Intrinsic Viscosity coPEN (70/0/30) Optical Layers, and Higher Intrinsic Viscosity coPEN (70/0/30) Non-optical Layers.

A multilayer reflective polarizer film may be constructed with first optical layers created from polyethylene naphthalate and second optical layers created from a low intrinsic viscosity (0.48 dL/g) co(polyethylene naphthalate) with carboxylate subunits derived from 70 mol % dimethyl naphthalene dicarboxylate and 30 mol % dimethyl isophthalate, and glycol subunits derived from 100 mol % ethylene glycol. The film also includes non-optical layers mad from a higher intrinsic viscosity (0.57 dL/g) co(polyethylene naphthalate) with carboxylate subunits derived from 70 mol % dimethyl naphthalene dicarboxylate and 30 mol % dimethyl isophthalate, and glycol subunits derived from 100 mol % ethylene glycol.

The polyethylene naphthalate used to form the first optical layers is synthesized in a batch reactor with the following raw material charge: 136 kg dimethyl naphthalene dicarboxylate, 73 kg ethylene glycol, 27 g manganese acetate, 27 g cobalt acetate, and 48 g antimony triacetate. Under pressure of 2 atm ($2\times10^5$ N/m$^2$), this mixture is heated to 254° C. while removing methanol (a transesterification reaction by-product). After 35 kg of methanol is removed, 49 g of triethyl phosphonoacetate is charged to the reactor and than the pressure is gradually reduced to 1 torr while heating to 290° C. The condensation reaction by-product, ethylene glycol, is continuously removed until a polymer with an intrinsic viscosity of 0.46 dL/g, as measured in 60/40 wt. % phenol/o-dichlorobenzene, is produced.

The co(polyethylene naphthalate) used to form the second optical layers is synthesized in a batch reactor with the following raw material charge: 109 kg dimethyl naphthalene dicarboxylate, 37 kg dimethyl isophthalate, 79 kg ethylene glycol, 29 g manganese acetate, 29 g cobalt acetate, and 58 g antimony triacetate. Under pressure of 2 atm ($2\times10^5$ N/m$^2$), this mixture is heated to 254° C. while removing methanol. After 41 kg of methanol is removed, 52 g of triethyl phosphonoacetate is charged to the reactor and than the pressure is gradually reduced to 1 torr while heating to 290° C. The condensation reaction by-product, ethylene glycol, is continuously stripped until a polymer with an intrinsic viscosity of 0.48 dL/g, as measured in 60/40 wt. % phenol/o-dichlorobenzene, is produced.

The co(polyethylene naphthalate) used to form the non-optical layers is synthesized in a batch reactor with the following raw material charge: 109 kg dimethyl naphthalene dicarboxylate, 37 kg dimethyl isophthalate, 79 kg ethylene glycol, 29 g manganese acetate, 29 g cobalt acetate, and 58 g antimony triacetate. Under pressure of 2 atm ($2\times10^5$ N/m$^2$), this mixture is heated to 254° C. while removing methanol. After 41 kg of methanol is removed, 52 g of triethyl phosphonoacetate is charged to the reactor and than the pressure is gradually reduced to 1 torr while heating to 290° C. The condensation reaction by-product, ethylene glycol, is continuously stripped until a polymer with an intrinsic viscosity of 0.57 dL/g, as measured in 60/40 wt. % phenol/o-dichlorobenzene, is produced.

The above described PEN and coPEN for the second optical layers may then be coextruded through multilayer melt manifolds to create a multilayer film with alternating first and second optical layers. This multilayer reflective film also contains internal protective layers and external protective layers made using the higher intrinsic viscosity co(polyethylene naphthalate) which are introduced through additional melt ports. This cast film is heated in an oven charged with hot air set at 145° C. for about one minute and the uniaxially oriented at a 6:1 draw to produce a reflective polarizer film of approximately 125 µm thickness.

Example 9

Polarizing Film with coPEN (85/15) Optical Layers, Low Intrinsic Viscosity coPEN (50/50) Optical Layers, and Higher Intrinsic Viscosity coPEN (50/50) Non-optical Layers.

A multilayer reflective polarizer film may be constructed with first optical layers created from co(polyethylene naphthalate) with carboxylate subunits derived from 85 mol % dimethyl naphthalene dicarboxylate and 15 mol % dimethyl terephthalate, and glycol subunits derived from 100 mol % ethylene glycol and second optical layers created from a low intrinsic viscosity (0.48 dL/g) co(polyethylene naphthalate) with carboxylate subunits derived from 50 mol % dimethyl naphthalene dicarboxylate and 50 mol % dimethyl terephthalate, and glycol subunits derived from 96.6 mol % ethylene glycol, 3 mol % 1,6-hexanediol, and 0.4 mol % trimethylol propane. The film also includes non-optical layers mad from a higher intrinsic viscosity (0.56 dL/g) co(polyethylene naphthalate) with carboxylate subunits derived from 50 mol % dimethyl naphthalene dicarboxylate and 50 mol % dimethyl terephthalate, and glycol subunits derived from 96.8 mol % ethylene glycol, 3 mol % 1,6-hexanediol, and 0.2 mol % trimethylol propane.

The co(polyethylene naphthalate) used to form the first optical layers is synthesized in a batch reactor with the following raw material charge: 123 kg dimethyl naphthalene dicarboxylate, 17 kg dimethyl terephthalate, 76 kg ethylene glycol, 27 g manganese acetate, 27 g cobalt acetate, and 48 g antimony triacetate. Under pressure of 2 atm ($2\times10^5$ N/m$^2$), this mixture is heated to 254° C. while removing methanol (a transesterification reaction by-product). After 36 kg of methanol is removed, 49 g of triethyl phosphonoacetate is charged to the reactor and than the pressure is gradually reduced to 1 torr while heating to 290° C. The condensation reaction by-product, ethylene glycol, is continuously removed until a polymer with an intrinsic viscosity of 0.48 dL/g, as measured in 60/40 wt. % phenol/o-dichlorobenzene, is produced.

The co(polyethylene naphthalate) used to form the second optical layers is synthesized in a batch reactor with the following raw material charge: 81.4 kg dimethyl naphthalene dicarboxylate, 64.5 kg dimethyl terephthalate, 82 kg ethylene glycol, 4.7 kg 1,6-hexanediol, 15 g manganese acetate, 22 g cobalt acetate, 15 g zinc acetate, 581 g trimethylol propane, and 48 g antimony triacetate. Under pressure of 2 atm ($2\times10^5$ N/m$^2$), this mixture is heated to 254° C. while removing methanol. After 44 kg of methanol is removed, 47 g of triethyl phosphonoacetate is charged to the reactor and than the pressure is gradually reduced to 1 torr while heating to 290° C. The condensation reaction by-product, ethylene glycol, is continuously stripped until a polymer with an intrinsic viscosity of 0.48 dL/g, as measured in 60/40 wt. % phenol/o-dichlorobenzene, is produced.

The co(polyethylene naphthalate) used to form the non-optical layers is synthesized in a batch reactor with the following raw material charge: 81.4 kg dimethyl naphthalene dicarboxylate, 64.5 kg dimethyl terephthalate, 82 kg ethylene glycol, 4.7 kg 1,6-hexanediol, 15 g manganese acetate, 22 g cobalt acetate, 15 g zinc acetate, 290 g trimethylol propane, and 48 g antimony triacetate. Under pressure of 2 atm ($2\times10^5$ $N/m^2$), this mixture is heated to 254° C. while removing methanol. After 44 kg of methanol is removed, 47 g of triethyl phosphonoacetate is charged to the reactor and than the pressure is gradually reduced to 1 torr while heating to 290° C. The condensation reaction by-product, ethylene glycol, is continuously stripped until a polymer with an intrinsic viscosity of 0.56 dL/g, as measured in 60/40 wt. % phenol/o-dichlorobenzene, is produced.

The above described coPENs for the first and second optical layers may then be coextruded through multilayer melt manifolds to create a multilayer film with alternating first and second optical layers. This multilayer reflective film also contains internal protective layers and external protective layers made using the higher intrinsic viscosity co(polyethylene naphthalate) which are introduced through additional melt ports. This cast film is heated in an oven charged with hot air set at 130° C. for about one minute and the uniaxially oriented at a 6:1 draw to produce a reflective polarizer film of approximately 125 μm thickness.

Example 10

A multi-layer reflective polarizer film was constructed with first optical layers created from polyethylenenaphthalate comprised of 100 mol % naphthalene dicarboxylate as the carboxylate, and 100 mol % ethylene glycol as the diol. Second optical layers were created from copolyethylenenaphthalate comprised of 55 mol % naphthalene dicarboxylate and 45 mol % terephthalate as carboxylates, and 95.8 mol % ethylene glycol, 4 mol % hexane diol, and 0.2 mol % trimethylol propane as glycols.

Polyethylenenaphthalate used to form the first optical layers was synthesized in a batch reactor with the following raw material charge; 136 kg dimethyl naphthalene dicarboxylate, 73 kg ethylene glycol, 27 grams manganese acetate, 27 grams cobalt acetate, and 48 g antimony tri-acetate. Under pressure of 2 atm, this mixture was heated to 254° C. while removing the transesterification reaction by-product methanol. After 35 kg of methanol was removed, 49 g of triethyl phosphonoacetate was charged to the reactor and than the pressure was gradually reduced to 1 torr while heating to 290° C. The condensation reaction by-product, ethylene glycol, was continuously removed until a polymer with an Intrinsic Viscosity of 0.48, as measured in 60/40 phenol/dichlorobenzene, was produced.

Copolyethylenenaphthalate used to form the second optical layers was synthesized in a batch reactor with the following raw material charge; 88.5 kg dimethyl naphthalene dicarboxylate, 57.5 kg dimethyl terephthalate, 81 kg ethylene glycol, 4.7 kg hexane diol, 29 grams cobalt acetate, 29 g zinc acetate, 239 g trimethylol propane, and 51 g antimony tri-acetate. Under pressure of 2 atm, this mixture was heated to 254° C. while removing the transesterification reaction by-product methanol. After 39.6 kg of methanol was removed, 56 g of triethyl phosphonoacetate was charged to the reactor and than the pressure was gradually reduced to 1 torr while heating to 290° C. The condensation reaction byproduct, ethylene glycol, was continuously stripped until a polymer with an Intrinsic Viscosity of 0.54, as measured in 60/40 Phenol/dichlorobenzene, was produced.

The above described CoPEN's were then coextruded through multi-layer die manifolds to create a multi-layer film with 836 alternating first and second optical layers. This particular multi-layer reflective film also contains internal protective layers and external protective layers comprised of the same copolyethylene naphthalate as the second optical layers. This cast film was then uniaxially oriented at a 6:1 draw after being heated to 163° C. to produce a reflective polarizer film of approximately 125 μm thickness.

When the described multi-layer reflective film was placed within an LCD computer display, the LCD display brightness increased by 56% which correlates to a "Gain" of 1.56. Increases in LCD display brightness are measured as Gain, which was the ratio of the brightness of an LCD display with brightness enhancing film to the brightness of an LCD display without the brightness enhancing film. Typically, the display brightness was measured with an LS-100 or LS-110 luminance meter. Interlayer adhesion in the above described multi-layer reflective was measured to be greater than 450 grams/inch (180 g/cm) using a standard 90 degree tape peel test.

Example 11

A multi-layer reflective polarizer film was constructed with first optical layers created from polyethylenenaphthalate comprised of 100 mol % naphthalene dicarboxylate as the carboxylate, and 100 mol % ethylene glycol as the diol. Second optical layers were created from copolyethylenenaphthalate comprised of 55 mol % naphthalene dicarboxylate and 45 mol % terephthalate as carboxylates, and 95.8 mol % ethylene glycol, 4 mol % hexane diol, and 0.2 mol % trimethylol propane as glycols. Thwas particular multi-layer film also contained external protective layers created from copolyethylenenaphthalate comprised of 75 mol % naphthalene dicarboxylate and 25 mol % terephthalate as carboxylates, and 95.8 mol % ethylene glycol, 4 mol % hexane diol, and 0.2 mol % trimethylol propane as glycols.

Polyethylenenaphthalate used to form the first optical layers was synthesized in a batch reactor with the following raw material charge; 136 kg dimethyl naphthalene dicarboxylate, 73 kg ethylene glycol, 27 grams manganese acetate, 27 grams cobalt acetate, and 48 g antimony tri-acetate. Under pressure of 2 atm, this mixture was heated to 254° C. while removing the transesterification reaction by-product methanol. After 35 kg of methanol was removed, 49 g of triethyl phosphonoacetate was charged to the reactor and than the pressure was gradually reduced to 1 torr while heating to 290° C. The condensation reaction by-product, ethylene glycol, was continuously removed until a polymer with an Intrinsic Viscosity of 0.48, as measured in 60/40 phenol/dichlorobenzene, was produced.

Copolyethylenenaphthalate used to form the second optical layers was synthesized in a batch reactor with the following raw material charge; 88.5 kg dimethyl naphthalene dicarboxylate, 57.5 kg dimethyl terephthalate, 81 kg ethylene glycol, 6.2 kg hexane diol, 29 grams cobalt acetate, 29 g zinc acetate, 239 g trimethylol propane, and 51 g antimony tri-acetate. Under pressure of 2 atm, this mixture was heated to 254° C. while removing the transesterification reaction by-product methanol. After 39.6 kg of methanol was removed, 56 g of triethyl phosphonoacetate was charged to the reactor and than the pressure was gradually reduced to 1 torr while heating to 290° C. The condensation reaction byproduct, ethylene glycol, was continuously stripped until a polymer with an Intrinsic Viscosity of 0.54, as measured in 60/40 phenol/dichlorobenzene, was produced.

Copolyethylenenaphthalate used to form the external protective layers was synthesized in a batch reactor with the following raw material charge; 114.8 kg dimethyl naphthalene dicarboxylate. 30.4 kg dimethyl terephthalate, 75 kg ethylene glycol, 5.9 kg hexane diol, 29 grams cobalt acetate, 29 g zinc acetate, 200 g trimethylol propane, and 51 g antimony tri-acetate. Under pressure of 2 atm, this mixture was heated to 254° C. while removing the transesterification reaction by-product methanol. After 39.6 kg of methanol was removed, 56 g of triethyl phosphonoacetate was charged to the reactor and than the pressure was gradually reduced to 1 torr while heating to 290° C. The condensation reaction byproduct, ethylene glycol, was continuously stripped until a polymer with an Intrinsic Viscosity of 0.52, as measured in 60/40 phenol/dichlorobenzene, was produced.

The above described CoPEN's were then coextruded through multi-layer die manifolds to create a multi-layer film with 836 alternating first and second optical layers. This particular multi-layer reflective film also contains internal protective layers comprised of the same copolyethylene naphthalate as the second optical layers. This cast film was then uniaxially oriented at a 6:1 draw after being heated to 160° C. to produce a reflective polarizer film of approximately 125 μm thickness.

When the described multi-layer reflective film was placed within an LCD computer display, the LCD display brightness increased by 58% which correlates to a "Gain" of 1.58. Increases in LCD display brightness are measured as Gain, which was the ratio of the brightness of an LCD display with brightness enhancing film to the brightness of an LCD display without the brightness enhancing film. Typically, the display brightness was measured with an LS-100 or LS-110 luminance meter.

Interlayer adhesion in the above described multi-layer reflective was measured to be greater than 450 grams/inch (180 g/cm) using a standard 90 degree tape peel test.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the present specification. The claims are intended to cover such modifications and devices.

We claim:

1. A multilayered polymer film, comprising:
   a plurality of first optical layers comprising a birefringent first copolyester; and
   a plurality of second optical layers comprising a second copolyester having an in-plane birefringence of about 0.04 or less, at 632.8 nm, after the multilayered polymer film has been formed, wherein the second copolyester comprises carboxylate subunits derived from trimellitic acid or an ester thereof.

2. The multilayered polymer film of claim 1, wherein the first copolyester comprises naphthalate subunits.

3. The multilayered polymer film of claim 1, wherein the second copolyester further comprises carboxylate subunits derived from cyclohexane dicarboxylic acid or an ester thereof.

4. The multilayered polymer film of claim 1, wherein the carboxylate subunits of the second copolyester further comprise naphthalate subunits.

5. The multilayered polymer film of claim 1, wherein the carboxylate subunits of the second copolyester further comprise terephthalate subunits.

6. The multilayered polymer film of claim 1, wherein the second copolyester further comprises glycol subunits derived from C2-C4 diols.

7. The multilayered polymer film of claim 1, wherein the second copolyester further comprises glycol subunits derived from 1,6-hexanediol or isomers thereof, trimethylol propane, or neopentyl glycol.

8. The multilayered polymer film of claim 1, wherein the first and second copolyesters both comprise naphthalate subunits.

9. A multilayered polymer film, comprising:
   a plurality of first optical layers consisting of polyethylenenaphthalate; and
   a plurality of second optical layers comprising a second copolyester having an in-plane birefringence of about 0.04 or less, at 632.8 nm, after the multilayered polymer film has been formed, the second copolyester comprising carboxylate subunits and glycol subunits, the carboxylate subunits comprising 20 to 100 mol % second carboxylate subunits and 0 to 80 mol % second comonomer carboxylate subunits, the glycol subunits comprising 40 to 100 mol % second glycol subunits and 0 to 60 mol % second comonomer glycol subunits, wherein 10 mol % or more of the combined carboxylate and glycol subunits of the second copolyester are second comonomer carboxylate subunits, second comonomer glycol subunits, or a combination thereof,
   wherein 0.01 to 2.5 mol % of the combined carboxylate and glycol subunits of the second copolyester are second comonomer carboxylate subunits derived from compounds having three or more carboxylate or ester functionalities, second comonomer glycol subunits derived from compounds having three or more hydroxy functionalities, or a combination thereof.

10. The multilayered film of claim 9 wherein the polyethylenenaphthalate is prepared from 100 mol % naphthalene dicarboxylate and 100 mol % ethylene glycol as the diol.

11. The multilayered film of claim 9 wherein the second copolyester comprises glycol subunits derived from 1,6-hexanediol.

12. The multilayer film of claim 9 wherein up to 30 mol % of glycol subunits of the second copolyester are derived from 1,6-hexanediol.

* * * * *